United States Patent
Matsui et al.

(10) Patent No.: US 9,429,507 B2
(45) Date of Patent: Aug. 30, 2016

(54) FLOW CELL, ANALYSIS EQUIPMENT AND ANALYSIS METHOD USING SAME

(71) Applicant: Hitachi High-Technologies Corporation, Minato-ku, Tokyo (JP)

(72) Inventors: Takuya Matsui, Tokyo (JP); Muneo Maeshima, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 65 days.

(21) Appl. No.: 14/390,276

(22) PCT Filed: Mar. 13, 2013

(86) PCT No.: PCT/JP2013/056895
§ 371 (c)(1),
(2) Date: Oct. 2, 2014

(87) PCT Pub. No.: WO2013/150869
PCT Pub. Date: Oct. 10, 2013

(65) Prior Publication Data
US 2015/0072350 A1    Mar. 12, 2015

(30) Foreign Application Priority Data
Apr. 3, 2012 (JP) ................................. 2012-084428

(51) Int. Cl.
| *G01N 21/75* | (2006.01) |
| *G01N 15/14* | (2006.01) |
| *C12M 1/34*  | (2006.01) |
| *C12M 1/00*  | (2006.01) |
(Continued)

(52) U.S. Cl.
CPC ..... *G01N 15/1404* (2013.01); *B01L 3/502753* (2013.01); *C12M 41/36* (2013.01); *C12M 47/02* (2013.01); *G01N 33/4833* (2013.01); *B01L 2300/0816* (2013.01); *B01L 2300/0877* (2013.01); *B01L 2400/0487* (2013.01); *B01L 2400/086* (2013.01); *G01N 2015/1006* (2013.01); *G01N 2015/1415* (2013.01)

(58) Field of Classification Search
CPC ..................... G01N 15/1404; G01N 33/4833; G01N 2015/1006; G01N 2015/1415; B01L 3/502753; B01L 2300/0816; B01L 2300/0877; B01L 2400/0487; B01L 2400/086; C12M 41/36; C12M 47/02
See application file for complete search history.

(56) References Cited

U.S. PATENT DOCUMENTS
2010/0003666 A1    1/2010 Lee et al.

FOREIGN PATENT DOCUMENTS
WO    WO 2009/130694 A2    10/2009

OTHER PUBLICATIONS
International Search Report dated May 28, 2013 with English translation (five (5) pages).
(Continued)

*Primary Examiner* — Dennis M White
(74) *Attorney, Agent, or Firm* — Crowell & Moring LLP

(57) ABSTRACT

All of bio-related substances, such as cells or bacteria, are placed at single and independent positions. A flow cell according to the present invention is used for analyzing a bio-related substance and includes a flow passageway and an injection opening and a discharge opening that are connected to the flow passageway. The flow passageway is provided with trapping structural members for trapping the bio-related substance. The trapping structural members include a structure forming a dead water region in which the bio-related substance is trapped.

16 Claims, 26 Drawing Sheets

(51) Int. Cl.
*B01L 3/00* (2006.01)
*G01N 33/483* (2006.01)
*G01N 15/10* (2006.01)

(56) References Cited

OTHER PUBLICATIONS

Nilsson et al., "Review of cell and particle trapping in microfluidic systems," Analytica Chimica Acta, 2009, vol. 649, pp. 141-157 (seventeen (17) pages).

Faley et al., "Cell chip array for microfluidic proteomics enabling rapid in situ assessment of intracellular protein phosphorylation," Biomicrofluidics, 2011, vol. 5, pp. 024106-1-024106-7 (seven (7) pages).

Kim et al., "Programmed trapping of individual bacteria using micrometer-size sieves," The Royal Society of Chemistry, 2011, vol. 11, pp. 1089-1095 (seven (7) pages).

Maennick et al, "Bacterial growth and motility in sub-micron constrictions," PNAS, 2009, vol. 106, No. 35, pp. 14861-14866 (twenty-three (23) pages).

Kim et al., "Building a better cell trap: Applying Lagrangian modeling to the design of microfluidic devices for cell biology," Journal of Applied Physics, 2008, vol. 103, pp. 044701-1-044701-7 (seven (7) pages).

Lutz et al, "Hydrodynamic Tweezers: 1. Noncontact Trapping of Single Cells Using Steady Streaming Microeddies," Anal. Chem., 2006, vol. 78, pp. 5429-5435 (seven (7) pages).

Japanese-language Written Opinion (PCT/ISA/237) dated May 28, 2013 with English translation (nine (9) pages).

German Office Action dated May 6, 2015 with English translation (seven pages).

FIG. 14
(a)
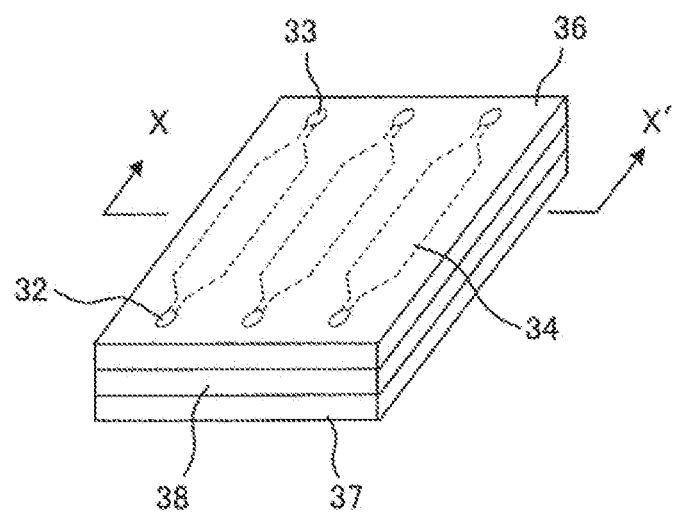
(b)
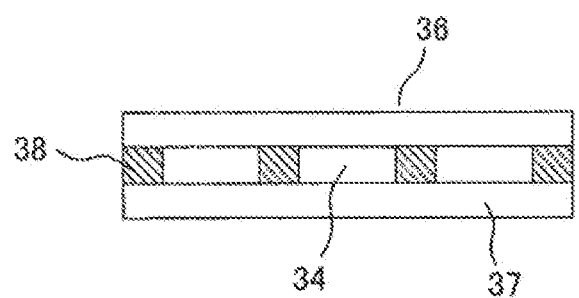

FIG. 28

| Trapped state | Probability | Details | Trapping example | Probability |
|---|---|---|---|---|
| Trapped singly | 0.63 (=1-0.37) | — | | 0.63 (=1-0.37) |
| Trapped in plural | 0.37 (Fig. 8) | Only two bacteria trapped in plural; rest trapped singly | | 0.20 (Fig. 9) (=0.37*0.75) |
| | | Only three bacteria trapped in plural; rest trapped singly | | 0.02 (Fig. 10) (=0.37*0.055) |
| | | Other | | 0.15 (=0.37-0.22) |

FLOW CELL, ANALYSIS EQUIPMENT AND ANALYSIS METHOD USING SAME

TECHNICAL FIELD

The present invention relates to a flow cell for performing analysis by sending a solution containing bio-related substances, such as cells or bacteria, to a device, and placing all of the substances at single and independent positions, an analysis device using the same, and an analysis method.

BACKGROUND ART

Generally, analysis of a bio-related substance, such as cells or bacteria, is conducted by a technique whereby the bio-related substance is multiplied by culturing, and then an average value of a number of bio-related substances is determined. Meanwhile, a method for analyzing single bio-related substances has been proposed in recent years, and researches on cell response or suppression mechanism, cell-cell interaction, and stem cell differentiation are being conducted. As a result, it has been established that an averaged behavior of a number of bio-related substances greatly differs from the behavior of single bio-related substances. In this method, a single bio-related substance can be analyzed, so that not only a bio-related substance of which multiplication by culturing is difficult or a small number of bio-related substances can be analyzed, but also an early analysis can be performed by omitting the multiplying step for a culturable bio-related substance. Thus, it can be expected that 99.9% of bacteria that are currently considered difficult to culture, and a small number of patient-derived cells, such as stem cells, or bacteria, can be analyzed early, and therefore the analysis of single bio-related substances is becoming increasingly more important. In recent years, identification of circulating tumor cell (CTC), which is a cancer cell present in blood, and bacteria is also being conducted.

In order to analyze the single bio-related substances, a plurality of bio-related substances needs to be placed at single and independent positions. The "independent positions" herein refer to positions such that single bio-related substances can be identified in the device for analyzing the substances. The method for placing the bio-related substances at the single and independent positions may be largely categorized into methods utilizing fluid dynamics, methods utilizing external forces, such as electricity, light, magnetism, or ultrasound, and methods utilizing a surface treatment or chemical coupling, as discussed in the review paper of Non Patent Literature 1. It should be noted here that, when the bio-related substances are placed, the phenotype of the bio-related substances should not be altered. For example, when the bio-related substance is placed by surface treatment or chemical coupling, there is the possibility of chemical change or structure change in the bio-related substance, resulting in analyzing the behavior of a different bio-related substance. Further, because the method using external force is difficult to control, it may be most desirable to use a bio-related substance placing method based solely on fluid dynamics. In the following, the outline and problems of a report of the bio-related substance placing method based on fluid dynamics will be described.

The most general method for analyzing single bio-related substances involves enclosing a solution containing the bio-related substance between a slide glass and a cover glass and observing the solution. According to a method, degeneration or nonspecific adsorption of the bio-related substance is prevented by using a slide glass coated with an agarose gel or a blocking agent (such as BSA or Casein). In another method, the solution containing the bio-related substance is sent to a flow passageway of a microchip and observed in a stationery state. By either method, the bio-related substances can be placed at single and independent positions by adjusting the concentration of the solution containing the bio-related substances. For example, a case is considered where 10 µl of a solution containing bio-related substances is enclosed in a gap (0.025 mm) between a slide glass and a cover glass (20 mm×20 mm). When it is desired to place the bio-related substances at average intervals of 1 mm, the solution containing the bio-related substances at the rate of $4 \times 10^4$/ml (40/µl) may be prepared. When it is desired to place the bio-related substances at average intervals of 0.1 mm, the solution containing the bio-related substances at the rate of $4 \times 10^6$/ml (4000/µl) may be prepared. However, in the above method, except for the case where the bio-related substances are nonspecifically adsorbed on the slide glass or the cover glass and the like, the position of the bio-related substances are irregularly changed by Brownian motion or the motility of the bio-related substances themselves, for example. Thus, once the bio-related substance is out of the observation field of view, it is difficult to identify the same bio-related substance again. Further, because the intervals of the bio-related substances are average values after all, the bio-related substances are not always present at the independent positions and may be adjacent to another bio-related substance (in this case, the analysis device cannot determine that the bio-related substances are adjacent to each other). Another problem is that it is difficult to follow the movement of the bio-related substances. Further, only a minute amount of solution (in the present case, 10 µl) containing the bio-related substances can be used for analysis.

In another method, a microtiter plate is used. In this method, in a microtiter plate having a number of microwells of sizes ranging from fL ($10^{-15}$ L) to pL ($10^{-12}$ L), a concentration-adjusted solution containing the bio-related substances is dispensed such that, probabilistically, one bacterium enters one microcell. By designing the size of the microwells to be slightly greater than the size of the bio-related substances to be placed, entry of a plurality of bio-related substances into the same microcell can be prevented. A report has been made where single cells (several dozen µm) were introduced into 80 to 90% of microwells using this method. However, when the size is small such as on the order of several µm, as in the case of, e.g., bacteria, the application may become more difficult if the shape is not spherical but bar-like and the substances themselves have motility. When the gap between the microwells and the cover glass is filled with liquid, the bacteria having motility may possibly flow out. Further, in order to replace the solution in the microwells, large amounts of fluid and time are required due to poor substitution efficiency, making recovery of the bio-related substances difficult. In addition, only a minute amount of solution containing the bio-related substances can be used for analysis.

According to a method for solving the problem of being capable of analyzing only a minute amount of solution containing the bio-related substances, the flow passageway of a microchip is provided with a structural member for trapping the bio-related substances, and the bio-related substances are trapped as the solution containing the bio-related substances flows. In this method, only a necessary amount of the bio-related substances can be sent in a solution, eliminating the need to adjust the concentration of the solution containing the bio-related substances, and making it possible to use a very thin solution. In the following, the outline and problems will be described with regard to a report of a bio-related substance placing method based on this method.

In Non Patent Literature 2, as the structural member for trapping CD 34 cell of approximately 10 μm, a basket-shaped trapping structural member provided with slits of several μm that are smaller than the cell at three locations is used. A solution containing a bio-related substance is sent and passed through the slit portions, whereby the solution is introduced into the basket-shaped trapping structural member. If the basket-shaped trapping structural member does not have the slits, it becomes difficult to flush out air (air bubbles) present before the solution is sent, which is not practical. As much of the solution containing the bio-related substance can be introduced into the basket-shaped trapping structural member as the amount of the solution containing the bio-related substance discharged from the slit portions. At this time, the introduced bio-related substances cannot pass the slits, so that the substance is trapped by the basket-shaped trapping structural member. Because the basket-shaped trapping structural member is of a similar size to the CD 34 cell, the probability of a plurality of CD 34 cells entering the same trapping structural member is lowered, whereby single CD 34 cells can be trapped in most of the trapping structural members. By varying the width or number of the slits of the trapping structural member, the ratio of the solution containing the bio-related substance that can be introduced into the trapping structural member can be varied, whereby the bio-related substance trap rate is changed. In this case, there are the following four problems. The first is that, while the bio-related substance of a known size can be trapped by setting the slit width smaller than the size, it is necessary to fabricate the slit with smaller width as the size of the bio-related substance becomes smaller. For example, while the CD 34 cell is approximately 10 μm, the minor axis of bacteria is approximately 0.5 to 1.0 μm. Because the value of the slit width design value to which a maximum process error of the slit is added must be smaller than the size of the bio-related substance, a high process accuracy on the order of 0.1 μm is required, resulting in an increase in manufacturing cost. Further, when a narrow width of slit is used, the bio-related substance trap rate is decreased. The second problem is that, while the probability of a plurality of bio-related substances being trapped by the same trapping structural member is lowered by making the size of the trapping structural member similar to that of the bio-related substance so that single bio-related substances can be trapped in most of the trapping structural members, when the size or shape of the bio-related substance is diverse, a plurality of bio-related substances may be trapped in one trapping structural member. For example, the lengths of bacteria include the minor axis (approximately 0.2 to 1.0 μm) the major axis (approximately 1 to 10 μm), thus extending in a wide range. The third problem is that, because not all of the bio-related substances can be trapped by the trapping structural member and only the trapped bio-related substances are used as the object for analysis, important information may be missed, or the number of the bio-related substances cannot be quantified. The fourth problem is that, as the bio-related substance is continuously subjected to the force pulling it into the slit portion, stress may be caused in the bio-related substance, possibly resulting in a change in phenotype. While it appears that in Patent Literature 1, the trapping structural member does not have a slit, there is a gap of 2 μm in the Z direction, thus providing the same function as the slits in Non Patent Literature 2.

In Non Patent Literature 3, using a trapping structural member having a slit of approximately 0.8 μm, a single *Escherichia coli* is trapped at different trapping structural member positions. As opposed to Non Patent Literature 2 or Patent Literature 1, the trapping structural member is made sufficiently larger in size than the bio-related substance, and the probability of trapping the bio-related substance is lowered so that, as a result, single bio-related substances can be trapped in the same trapping structural member. However, there are the following problems. The first is that *Escherichia coli* of 0.8 μm or smaller is not trapped. Non Patent Literature 4 also reports that *Escherichia coli* can pass a flow passageway of a size one half its own minor axis, depending on the condition. In this case, even *Escherichia coli* of 1.6 μm may pass depending on the condition. The second problem is that not all of the bio-related substances can be trapped by the trapping structural member, and no analysis of the conditions is conducted. The third problem is that, as the bio-related substance is continuously subjected to the force pulling it toward the slit portion, stress may be caused in the bio-related substance, possibly resulting in a change in phenotype. The fourth problem is that, as discussed in Non Patent Literature 3, when the solution is sent at high speed, the bacteria may possibly be dissolved.

CITATION LIST

Patent Literature

Patent Literature 1: US2010/0003666

Non Patent Literature

Non Patent Literature 1: Analytica Chimica Acta 649 (2009) 141-157
Non Patent Literature 2: Biomicrofluidics 5, 024106 (2011)
Non Patent Literature 3: Lab Chip, 2011, 11, 1089
Non Patent Literature 4: PNAS, 2009, 106, 14861-66

SUMMARY OF INVENTION

Technical Problem

To summarize the background technology, in order to place all of the bio-related substances, such as cells or bacteria, at single and independent positions, the following problems must be addressed.
1. The smaller the bio-related substance the narrower the width of a slit fabricated must be.
   Fabrication of a slit with narrow width leads to an increase in manufacturing cost. Further, when a slit of narrow width is used, the bio-related substance trap rate is lowered. When the trapping structural member does not have a slit, it becomes difficult to flush out air (air bubbles) present prior to sending the solution.
2. Because the bio-related substance is trapped with a slit, external force is applied, causing stress.
   When the bio-related substance is subjected to stress, there is the possibility of a change in phenotype. Also, force from flow field may be generated in the bio-related substance held in the slit.
3. When the solution is sent at high speed, the bio-related substance may possibly be dissolved.
   Some of the problems may be partially solved by the methods described with reference to the background technology, but not all of the problems can be solved. The present invention provides an analysis device capable of addressing all of these requirements.

Solution to the Problem

A flow cell according to the present invention is a flow cell used for analyzing a bio-related substance which includes a flow passageway and an injection opening and a discharge opening that are connected to the flow passageway. The flow passageway is provided with trapping structural members for trapping the bio-related substance. The trapping structural members include a structure forming a dead water region in which the bio-related substance is trapped.

Advantageous Effects of Invention

A solution containing the bio-related substance, such as a cell or a bacterium, can be sent to a device, placed at single and independent positions, and analyzed. Problems, configurations, and effects other than those mentioned above will become apparent from the following description of embodiments.

BRIEF DESCRIPTION OF DRAWINGS

FIG. 14 is a schematic diagram of an example of a flow cell.

FIG. 28 is a table showing the probability computed for each trap state when the #Trapped bacteria ($1^{st}$ column) is 10 and the #Trap object (Column) is 100.

DESCRIPTION OF EMBODIMENTS

In the following, embodiments of the present invention will be described with reference to the drawings. The present invention can be generally applied to an analysis device of a system such that a plurality of bio-related substances are placed at single and independent positions for analysis. In the following, an example in which the present invention is applied to a bacterial analysis will be described.

Figure 1:
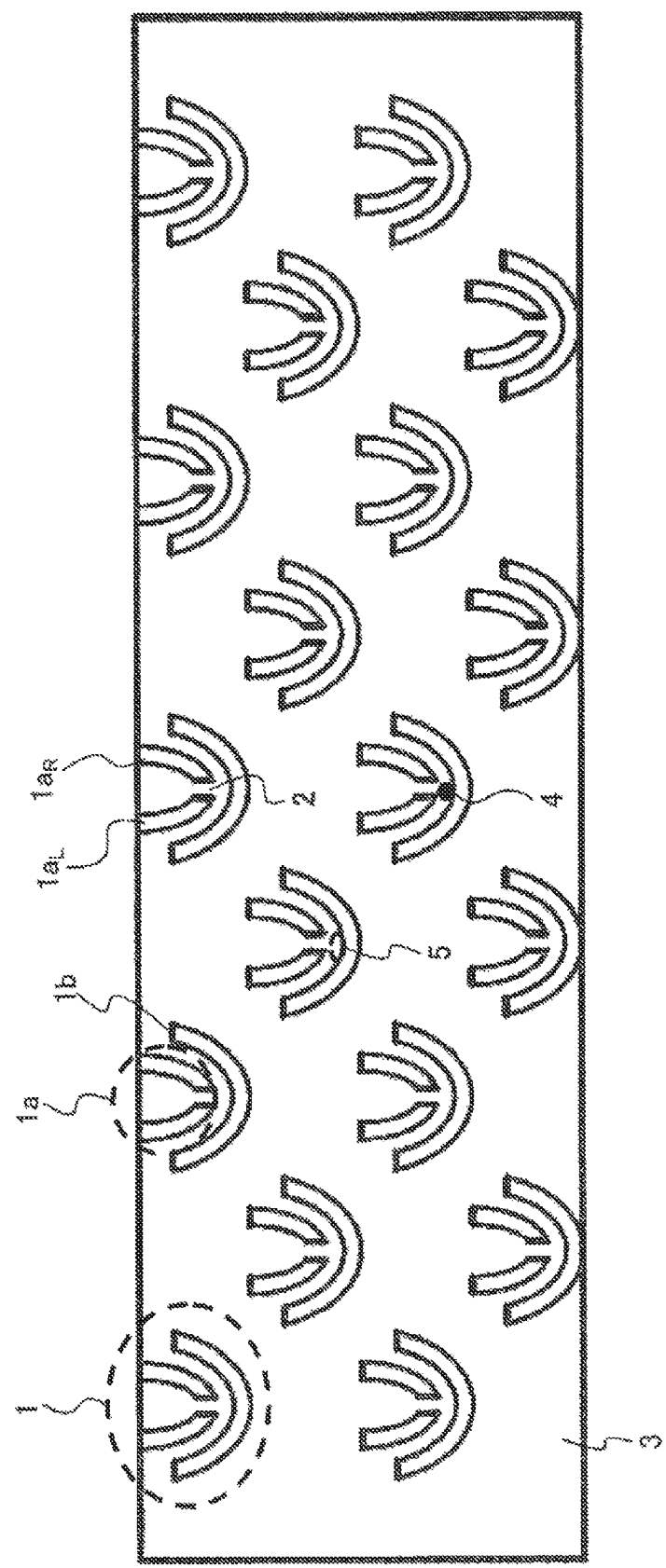
FIG. 1 is a schematic diagram of an example of a trapping structural member.

FIG. 1 is a schematic diagram of an example of trapping structural members according to the present invention. The trapping structural members 1 are structural members including a pair of a structural member 1a with a slit and a structural member 1b without a slit, and a plurality of the trapping structural members 1 are disposed. The structural member 1a with a slit includes a left side $1a_L$, of the structural member with a slit and a right side $1a_R$ of the structural member with a slit, with a slit 2 disposed between the sides. A solution (not shown) containing bio-related substances 4 is injected via an injection opening (see FIG. 14) located the top of FIG. 1, sent via a flow passageway 3, and discharged out of a discharge opening (see FIG. 14) disposed at the bottom of FIG. 1. The trapping structural members 1 have a height equal to the height of the flow passageway. In this process, the solution, not shown, containing the bio-related substances 4 flows into the structural member 1a with a slit with a certain probability, passes the slit 2, and flows out of gaps at two locations between the structural member 1a with a slit and the structural member 1b without a slit. At this time, the bio-related substances 4 are trapped in a dead water region 5 with a certain probability. The dead water region 5 is a region where there is no flow or a region where the flow, if any, is whirling and that has nothing to do with the canalization of flow volume. The bio-related substances 4 that has passed the slit 2 are trapped in the dead water region 5 with a certain probability by diffusion, inertial force, or their motility. The dead water region 5 is formed in a region such as a sharply expanding portion, a sharply contracted portion, or a curved portion. The dead water region 5 can be expanded by structural optimization, such as by providing the structural member 1b without a slit with a recess near the dead water region. The bio-related substances 4 trapped in the dead water region 5 are hardly subject to the force of the fluid. Thus, no stress is caused in the bio-related substances 4, nor is the substance dissolved. The structural member 1b without a slit is present on the downstream side of the dead water region 5. Thus, even if the bio-related substances 4 are small, the bio-related substances 4 do not flow from the dead water region 5 toward the downstream side. Because the structural member 1a with a slit has the function of filling the flow passageway of the structural member 1b without a slit with the solution containing the bio-related substances 4 from the downstream side to the upstream side via the slit 2, air bubbles can be readily removed. While the structural bar 1a with a slit and the structural member 1b without a slit each comprise a part of an elliptic arc, they may comprise a part of an arc or a triangle. Different shapes of the structural members produce differences in flow, which in turn lead to differences in the bio-related substance 4 trap rate.

FIG. 2A illustrates the result of a flow simulation where the trapping structural member was placed at the center of a flow passageway with a width of 1 mm, and the solution was sent from the left side toward the right side at the flow velocity of 1 mm/s. The slit width was 5 μm. FIG. 2B is an enlarged view of the region of the trapping structural member, the direction of the flow of solution being indicated by arrows. As illustrated, the solution that has passed the slit flows out toward the gaps at the two locations between the structural member 1a with a slit and the structural member 1b without a slit in a branched manner. Thus, the dead water region is formed at the branching region.

FIG. 3A illustrates the result of a flow simulation where the trapping structural members are placed at a portion shifted from the center of the flow passageway with the width of 1 mm, and the solution was sent from the left side toward the right side at the flow velocity of 1 mm/s. The slit width was 5 μm. FIG. 3B is an enlarged view of the region of the trapping structural member, with the direction of flow of the solution being indicated by arrows. As illustrated, the solution that has passed the slit flows out toward one of the two locations of the gaps between the structural member 1a with a slit and the structural member 1b without a slit. There is also a flow formed from one of the gaps toward the other gap. Because there is no branching region in contrast with FIG. 2, the dead water region is not formed.

FIG. 4A illustrates the result of a flow simulation where the trapping structural member was placed at a portion shifted from the center of the flow passageway with the width of 1 mm, and the solution was sent from the left side toward the right side at the flow velocity of 1 mm/s. The conditions were the same as those of FIG. 3 with the exception that the slit width was 30 μm. FIG. 4B is an enlarged view of the region of the trapping structural member, the direction of flow of the solution being indicated by arrows. As illustrated, the solution that has passed the slit flows out toward the gaps at the two locations between the structural member 1a with a slit and the structural member 1b without a slit in a branched manner. In contrast with the case of FIG. 3, the dead water region is formed at the branching region. Accordingly, the structural member having the slit has the advantage that the dead water region can be formed by adjusting parameters such as the slit width.

Figure 2:
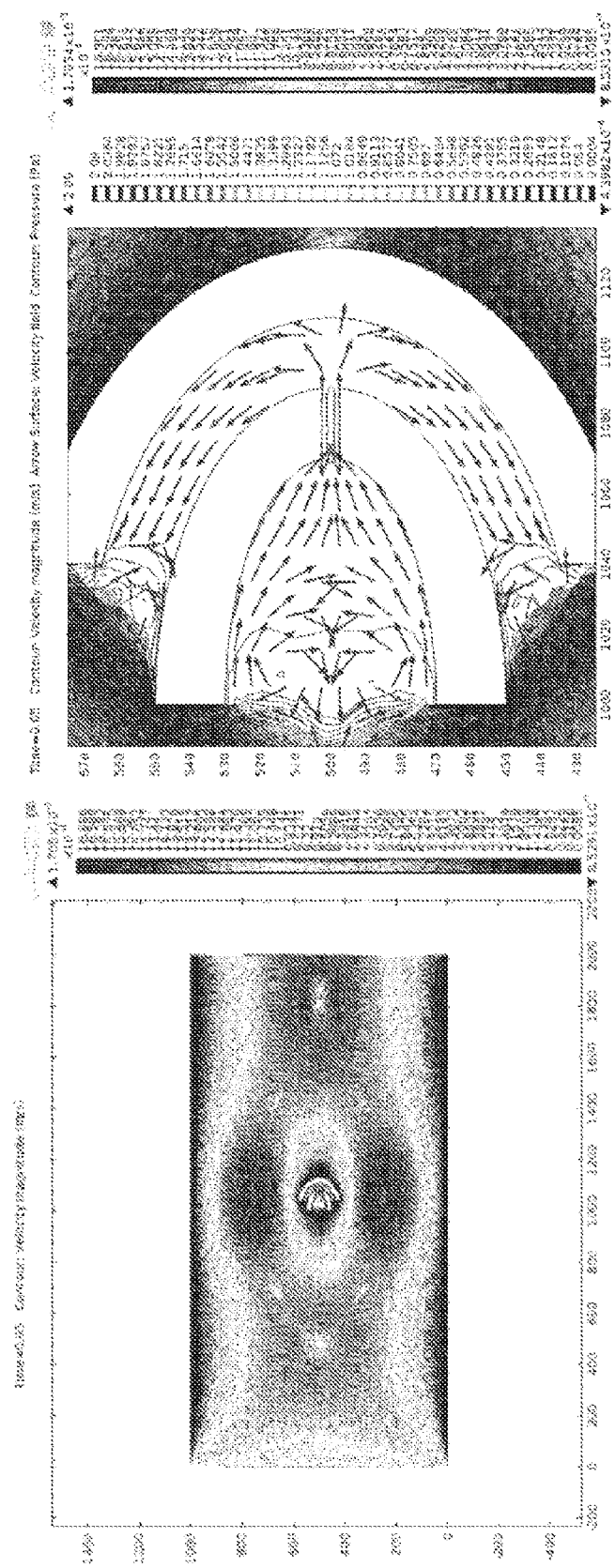
FIG. 2 illustrates an example of simulation of flow into the trapping structural member.
Figure 3:
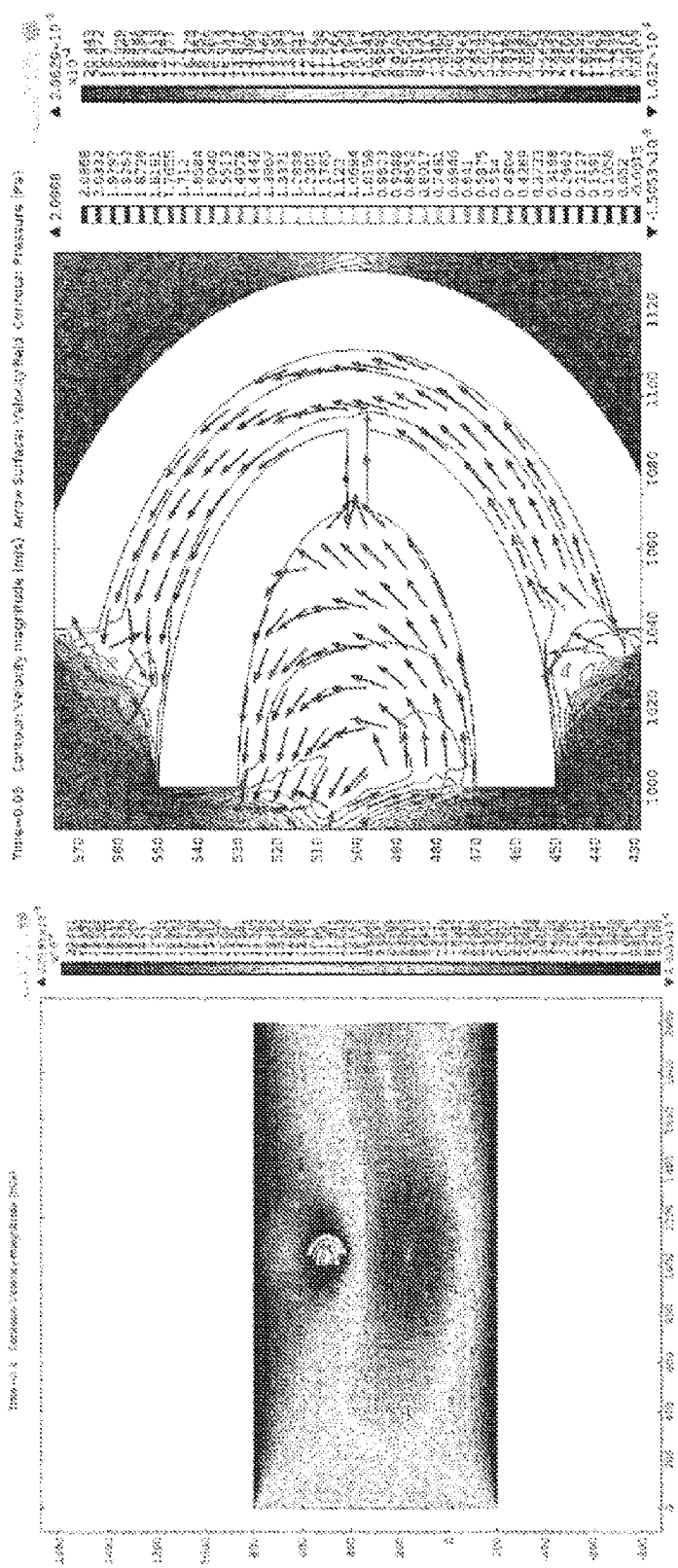
FIG. 3 illustrates an example of simulation of flow into the trapping structural member.
Figure 4:
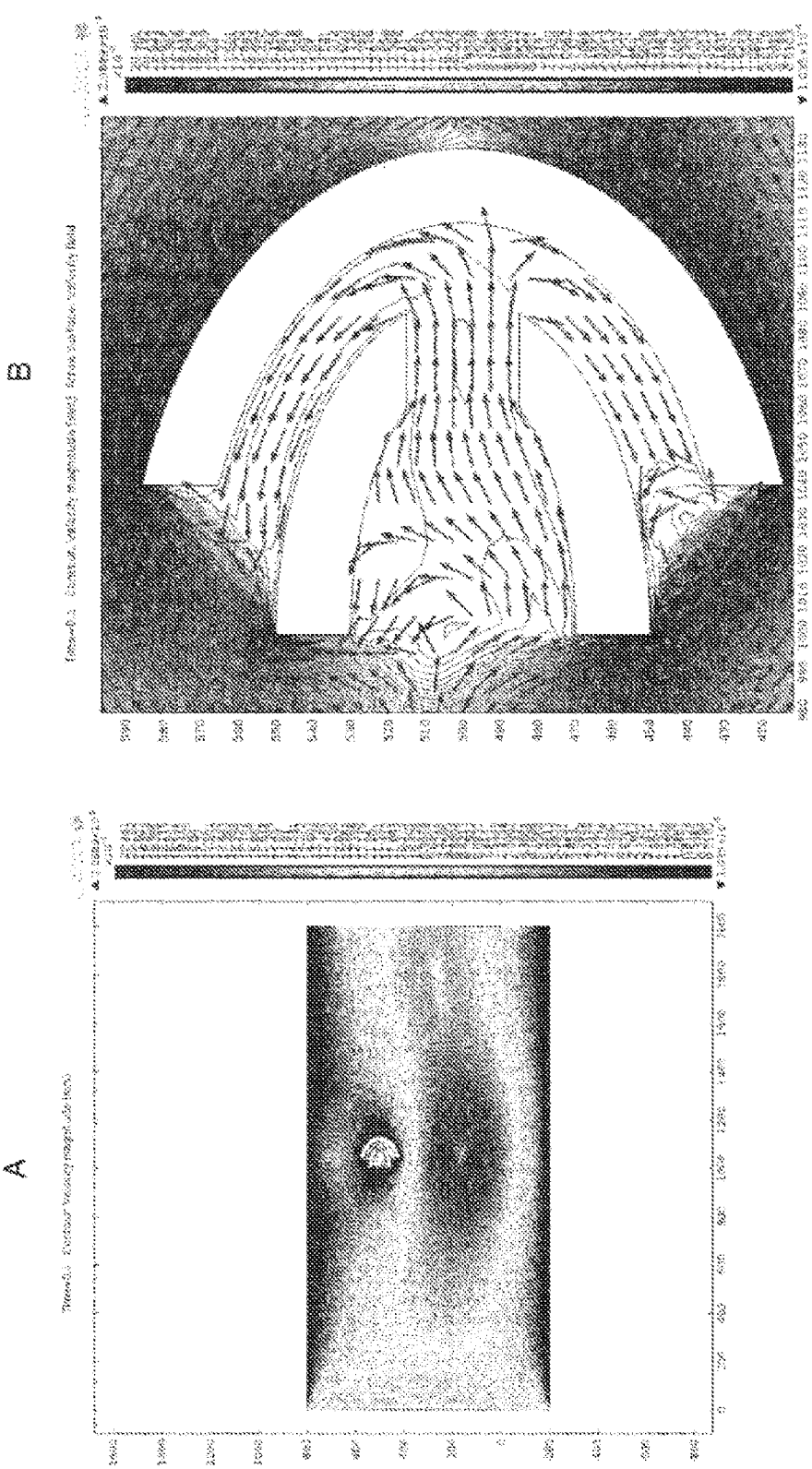
FIG. 4 illustrates an example of simulation of flow into the trapping structural member.

Conditions for trapping all of the bio-related substances will be described. First, the trap rate (/one trapping structural member) of the bio-related substances in the trapping structural members is computed by [α: (flow volume of flow into the trapping structural member)/(total flow volume)]×[β: the bio-related substance trap rate in the trapping structural member]. While β is in the range of 0 to 1, if it is assumed that β=1 (i.e., all of the bio-related substances that have flowed into the trapping structural member are trapped) by adjusting the parameters, the trap rate (/one trapping structural member) can be approximated by α. Obviously, α may be multiplied by a safety coefficient. Thus, the trap rate (/one trapping structural member) can be computed by [(the slit width)×(average flow velocity in the slit)]/[(the flow passageway width)/(average flow velocity in the flow passageway)]. In the example of FIG. 3, the trap rate (/one trapping structural member) is computed by [(0.005 mm)/(0.0004 mm/s)]/[(1 mm)/(1 mm/s)], which is 0.000002. This indicates the probability that of one million of the bio-related substances, two can be trapped in the trapping structural members. Similarly, in the example of FIG. 4 where only the slit width is changed from 5 μm of FIG. 3 to 30 μm, the trap rate (/one trapping structural member) is [(0.03 mm)/(0.0016 mm/s)]/[(1 mm)/(1 mm/s)] equals 0.00005, which is approximately 25 times greater. Thus, the structural member having the slit has the advantage that the trap rate (/one trapping structural member) can be adjusted by adjusting parameters such as the interval of the trapping structural members, the slit width, the flow passageway width, or flow velocity. For example, by simply changing the flow passageway width of 1 mm in FIG. 4 to 0.36 mm, the trap rate (/one trapping structural member) can be increased to 0.001. However, as illustrated in FIG. 2 to FIG. 4, while the solution containing the bio-related substances has its flow direction changed immediately before entry into the trapping structural member, the direction cannot be changed sharply because of inertial force acting on the bio-related substances, whereby the solution readily flows into the trapping structural member. Thus, the actual trap rate (/one trapping structural member) becomes higher than the computed result of the flow volume ratio. Accordingly, because the faster the flow velocity, the greater the inertial force that acts, the actual trap rate (/one trapping structural member) becomes higher.

Figure 5:
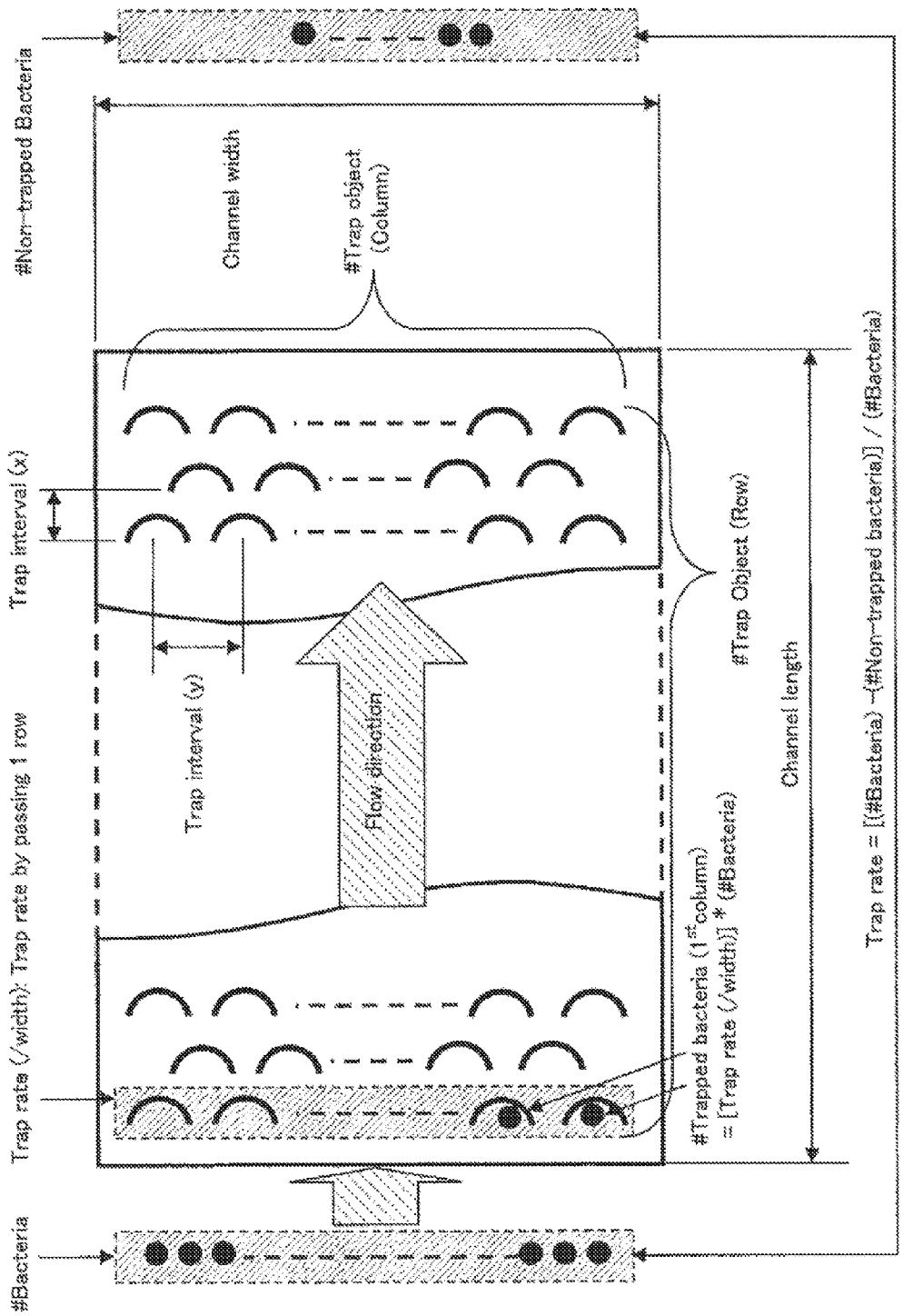
FIG. 5 is a schematic diagram concerning parameters for trapping all of the bio-related substances.

FIG. 5 illustrates the parameters for computing the conditions for trapping all bacteria. If the trap rate per trapping structural member is known, the conditions for trapping all of the bio-related substances can be computed. The #Bacteria is the number of bacteria before being sent to the trapping structural members. The #Non-trapped Bacteria is the number of bacteria after being sent to the trapping structural members. The solution sending direction is indicated by the arrow Flow direction. The Trap rate is the ratio of bacteria trapped in the trapping structural members and computed by [(#Bacteria)−(#Non-trapped Bacteria)]/(#Bacteria). The trapping structural members are indicated schematically by semicircular arcs, with the intervals between the adjacent trapping structural members indicated by Trap interval (x) and Trap interval (y), the x-direction being parallel with the solution sending direction and the y-direction being vertical with respect to the x-direction. The #Trap Object (Column) is the number of trapping structural members arranged in the y-direction, and the #Trap Object (Row) is the number of trapping structural members arranged in the x-direction. The Channel length is the length of the flow passageway in which the trapping structural members are formed in the solution sending direction (the x-direction), and the length is computed by Trap interval (x)×#Trap Object (Row). Similarly, the Channel width is the length of the flow passageway in which the trapping structural members are formed in the y-direction, and the length is computed by Trap interval (y)×#Trap Object (Column). The Trap rate (width) indicates the trap rate when one column of the trapping structural members placed in the y-direction is passed. The #Trapped bacteria (1st column) is the number of bacteria trapped by the trapping structural members in the first column, and is computed by [Trap rate (/width)]× (#Bacteria). The #Trapped bacteria (1st column) becomes smaller as the number of the columns of the passed trapping structural members increases. The Trap rate (/width) is equal to the trap rate (/one trapping structural member) when the flow passageway width is Trap interval (y) in FIG. 2 to FIG. 4. This is because the trap rate of the trapping structural members per Trap interval (y) is the same as the trap rate when a plurality of the trapping structural members is arranged in parallel.

Figure 6:
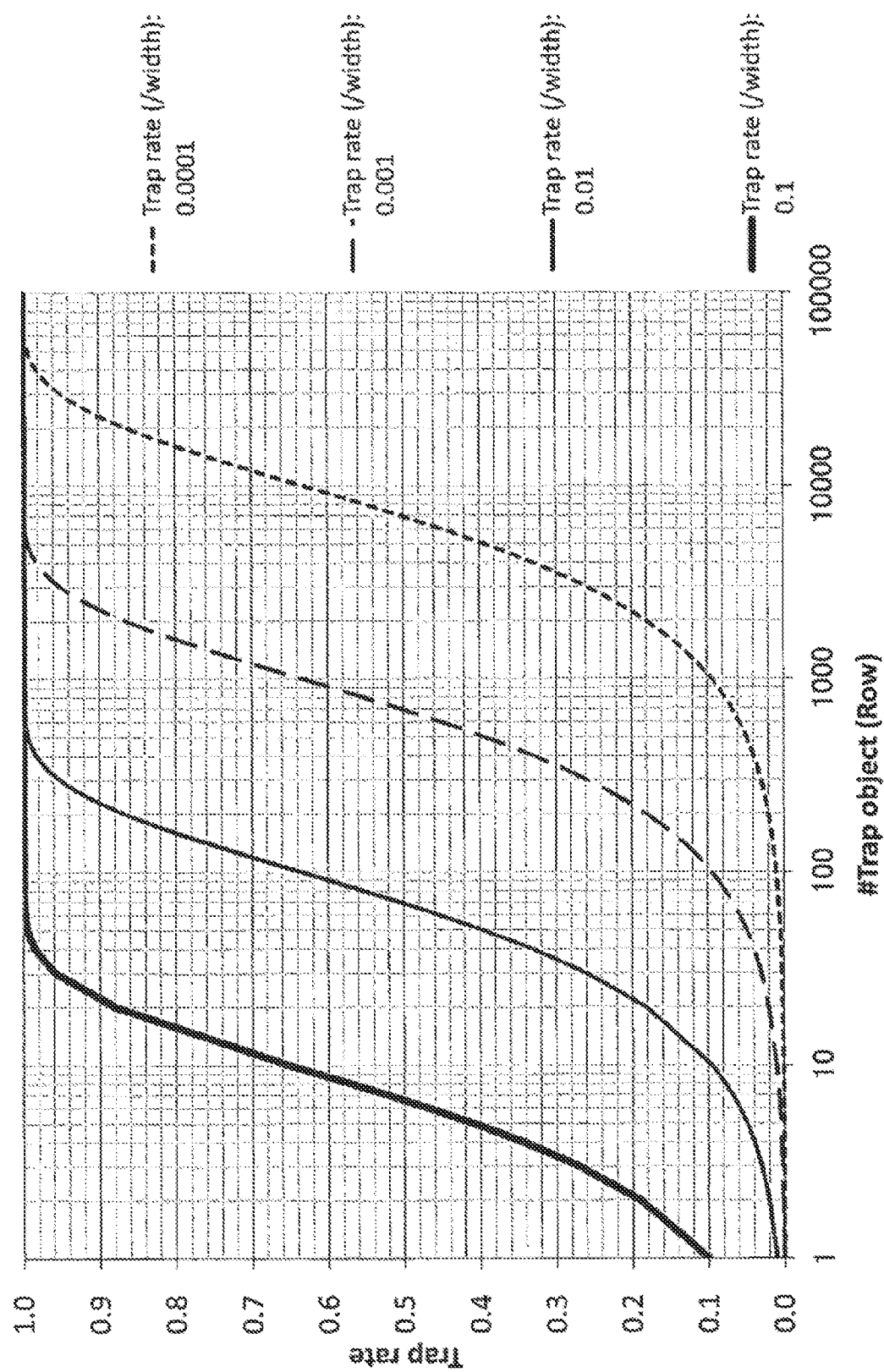
FIG. 6 illustrates the trap rate and the number of trapping structural members (solution sending direction).

FIG. 6 illustrates the relationship between Trap rate and #Trap object (Row) in the case of Trap rates (/width) of 0.0001 to 0.1. When the Trap rate (/width) is 0.01, the number of columns of the trapping structural members that need to be placed in the solution sending direction (the x-direction) is 300 for the trap rate of 95%, 470 for the trap rate of 99%, and 700 for the trap rate of 99.9%. When the Trap rate(/width) is 0.001, the number of the trapping structural members that need to be placed in the solution sending direction (the x-direction) is 3000 for the trap rate of 95%, 4700 for the trap rate of 99%, and 7000 for the trap rate of 99.9%.

Figure 7:
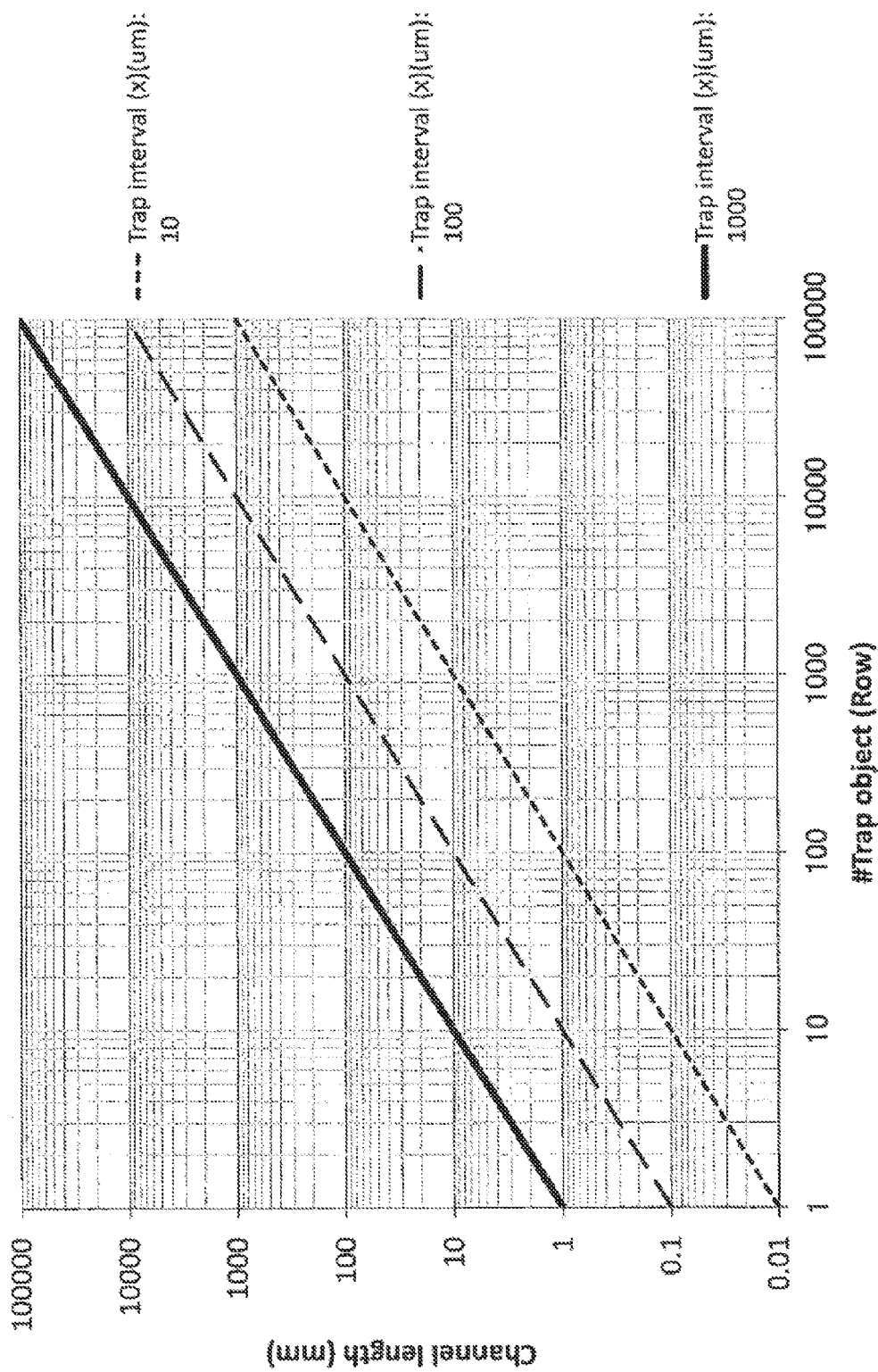
FIG. 7 illustrates the number of trapping structural members (solution sending direction) and the channel length.

FIG. 7 illustrates the relationship between #Trap object (Row) and Channel length (mm) in the case of Trap interval (x) of 10 to 1000 μm. When the Trap interval (x) is 100 μm, the Channel length required is 70 mm when 700 columns of the trapping structural members for trapping 99.9% with the Trap rate (/width) of 0.01 are placed, or 700 mm when 7000 columns of the trapping structural members for trapping 99.9% at the Trap rate (/width) of 0.001 are placed. Considering that the upper limit of the size of a general microchip permitting easy handling by a user is the size of a postcard (100 mm×150 mm), a meandering flow passageway and the like is required in order to realize the Channel length of 700 mm. In order to estimate the maximum #Trap object (Row), the minimum trapping structural member size for trapping bacteria is determined to determine the minimum Trap interval (x). The maximum Channel length value including the meandering flow passageway and the like may be determined and then divided by the minimum Trap interval (x) for calculation.

The conditions for placing all bacteria at single and independent positions will be described, When the #Trapped bacteria (1st column) is one or smaller, all bacteria can be placed at single and independent positions. Because the #Trapped bacteria (1st column) is [Trap rate (/width)]× (#Bacteria), the Trap rate (/width) may be 1/#Bacteria or smaller. For example, when the #Bacteria is 1000, all bacteria can be placed at single and independent positions by making the Trap rate (/width) 0.001 or smaller. When the #Bacteria is not known, the #Trapped bacteria (1st column) may become greater than one, whereby a plurality of bacteria may be trapped in the same trapping structural member. In this case, it is possible to make the #Trapped bacteria (1st column) one or smaller by decreasing the #Trapped bacteria (1st column) by dividing the solution containing the #Bacteria, or by designing the Trap rate (/width) to be sufficiently small. FIG. 28 shows the probability computed for each trap state when the #Trapped bacteria (1st column) is 10 and the #Trap object (Column) is 100. In the trap example column, the semicircle indicates the trapping structural member, and the black dot (●) indicates the trapped bacteria.

Figure 8:
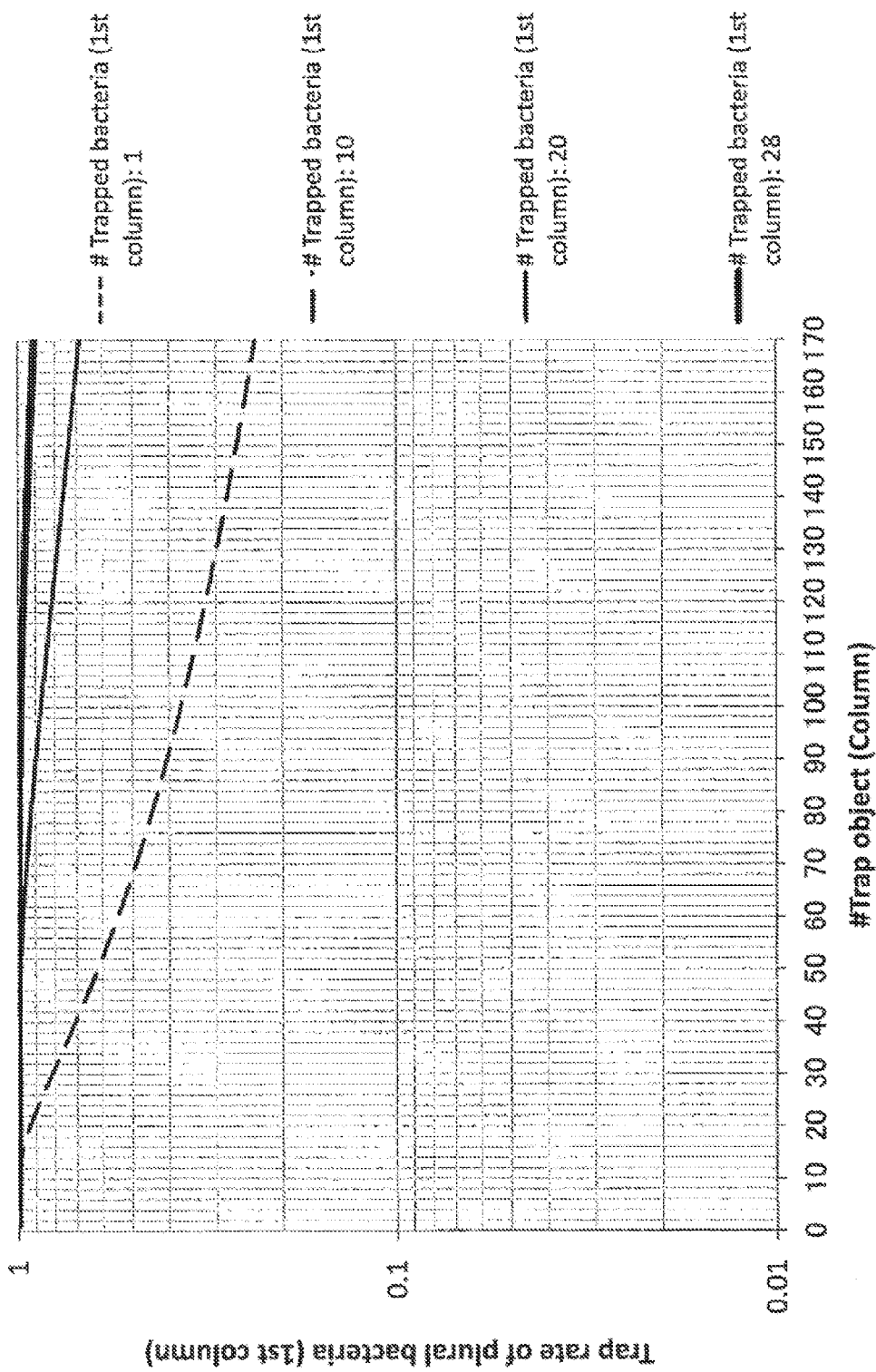
FIG. 8 illustrates the probability of at least two or more bio-related substances being trapped in the same trapping structural member.

FIG. 8 illustrates the relationship between the #Trap object (Column) and the probability of at least two or more bacteria being trapped in the same trapping structural member in the case of the #Trapped bacteria (1st column) of 1 to 28. When the #Trapped bacteria (1st column) is 10 and the #Trap object (Column) is 100, at least two or more bacteria are trapped in the same trapping structural member with the probability of 0.37 (37%).

Figure 9:
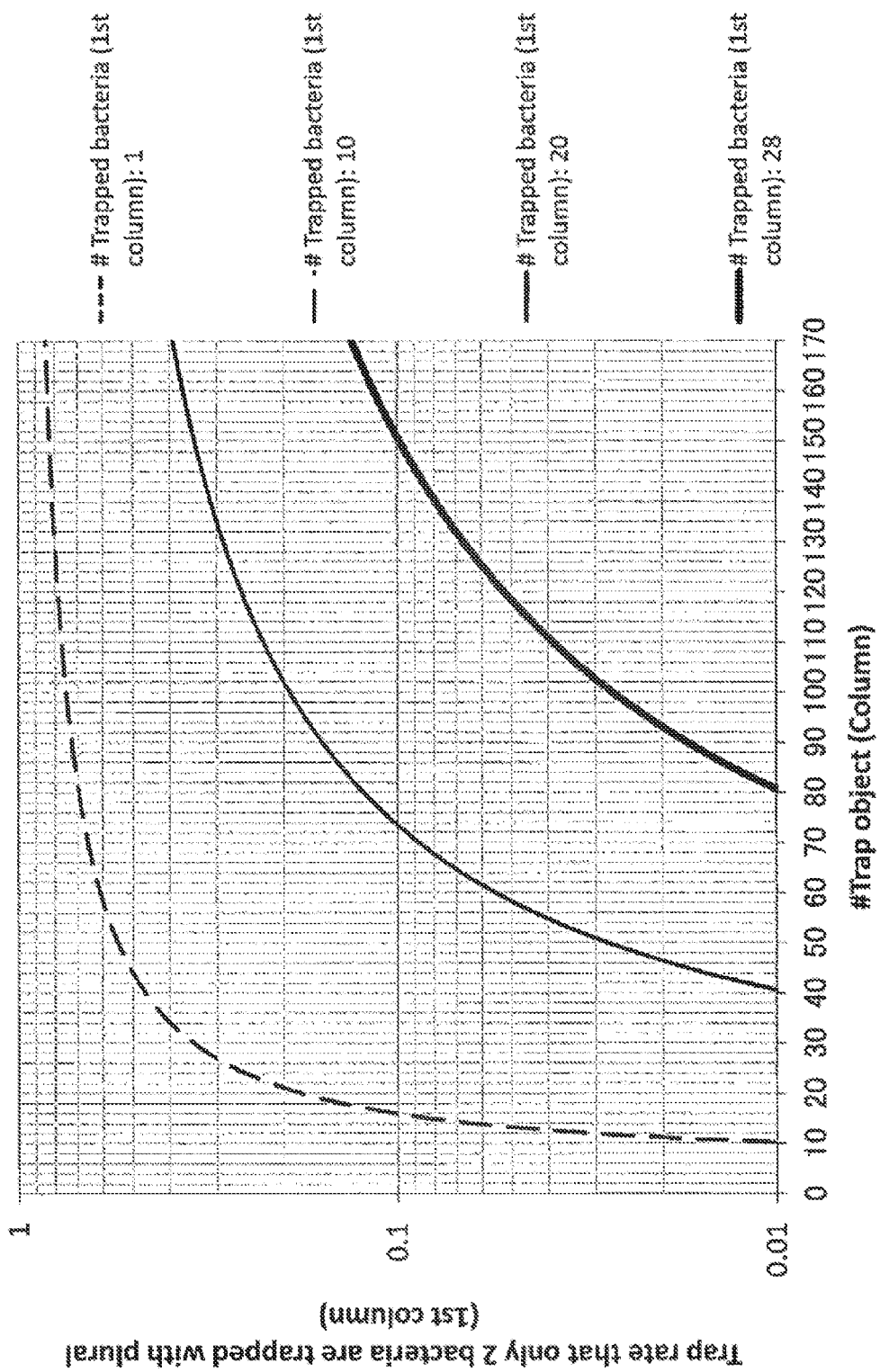
FIG. 9 illustrates the probability of two bio-related substances being trapped in the same trapping structural member.

FIG. 9 illustrates the relationship between the #Trap object (Column) and the probability of only two bacteria being trapped in the same trapping structural member in the case of the #Trapped bacteria (1st column) of 1 to 28. When the #Trapped bacteria (1st column) is 10 and the #Trap object (Column) is 100, only two bacteria are trapped in the same trapping structural member with the probability of 0.75(75%). Because the probability of multiple trappings is 0.37, the probability of only two bacteria being trapped in the same trapping structural member is 0.20 (=0.37×0.75). In this case, the remaining eight bacteria. are singly trapped in the trapping structural members.

Figure 10:
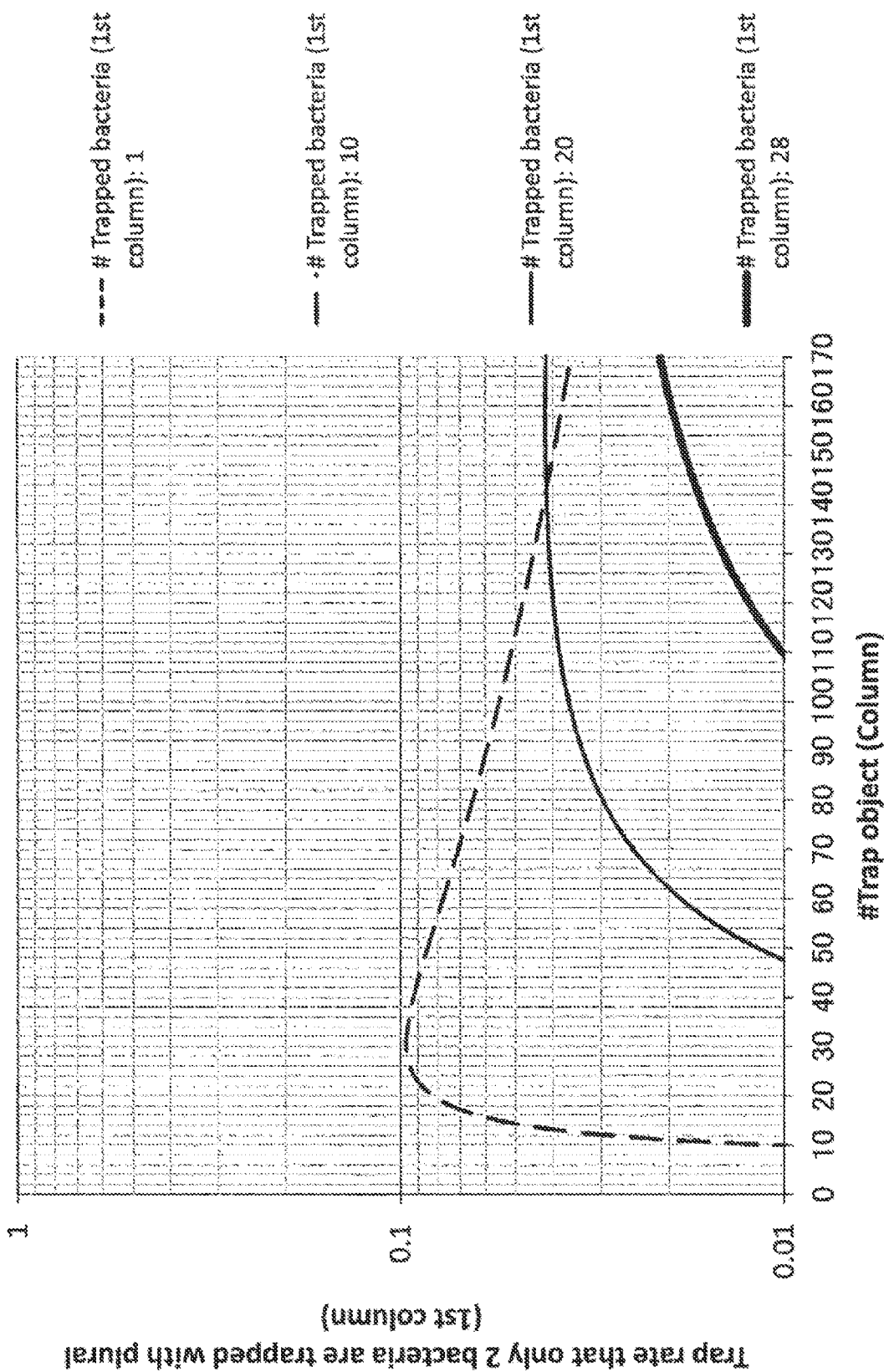
FIG. 10 illustrates the probability of three bio-related substances being trapped in the same trapping structural member.

FIG. 10 illustrates the relationship between the #Trap object (Column) and the probability of only three bacteria being trapped in the same trapping structural member in the case of the #Trapped bacteria (1st column) of 1 to 28. When the #Trapped bacteria (1st column) is 10 and the #Trap object (Column) is 100, only three bacteria are trapped in the same trapping structural member with the probability of 0.055 (5.5%). Because the probability of multiple trappings is 0.37, the probability of only three bacteria being trapped in the same trapping structural member is 0.02 (=0.37× 0.055). In this case, the remaining seven bacteria are singly trapped in the trapping structural members. Thus, when the #Trapped bacteria (1st column) is 10 and the #Trap object (Column) is 100, the probability of two or more bacteria being trapped in the same trapping structural member is 0.37, of which the probability of only two bacteria being trapped in the same trapping structural member is 0.20 and the probability of only three bacteria being trapped in the same trapping structural member is 0.02. Therefore, the probability of four or more bacteria, being trapped in the same trapping structural member is 0.15[=0.37−(0.20+ 0.02)]. The greater the #Trapped bacteria (1st column) or the smaller the #Trap object (Column), the greater the probability of a plurality of bacteria being trapped in the same trapping structural member becomes.

The effects of the present invention are as follows.

1. The concentration of the bacteria-containing solution needs to be adjusted.

The structural members for trapping bacteria are disposed in the flow passageway of the microchip, and the trapping is performed while a bacteria-containing solution flows. Because only a necessary amount of the bacteria-containing solution can be sent, there is no need for adjusting the concentration of the bacteria-containing solution, and a very thin solution can be used.

2. The smaller the bacteria, the narrower the width of the slit fabricated needs to be.

Because the bacteria trapping principle is not based on a slit, there is no need to fabricate a narrow width slit.

3. Not all bacteria can be trapped.

By computing the trap rate per trapping structural member, the number of trapping structural members for trapping all bacteria can be calculated.

4. Because bacteria are trapped with a slit, external force is applied and stress is caused.

Instead of trapping bacteria in a slit, bacteria are trapped in a dead water region, so that no external force is applied.

5. A plurality of bacteria are trapped in one trapping structural member.

By making the #Trapped bacteria (1st column) one or smaller, the trapping of a plurality of bacteria in one trapping structural member can be avoided.
6. When the solution is sent at high speed, there is the possibility of dissolution of the bacteria.

Because the bacteria are trapped in the dead water region, no external force is applied from the fluid.

Further, because the present invention provides the structural member comprising a pair of a structural member with a slit and a structural member without a slit, the following three advantages can be obtained.
1. The structural member with a slit makes it possible to fill the flow passageway of the structural member without a slit with the solution from the downstream side to the upstream side via the slit, facilitating the removal of air bubbles.
2. The structural member with a slit enables the formation of a dead water region by adjusting parameters such as the slit width.
3. The structural member with a slit makes it possible to change the trap rate by adjusting parameters such as the intervals between the trapping structural members, slit width, or flow velocity. By increasing the trap rate, all of bio-related substances can be trapped. While the slit 2 is disposed at one location in FIG. 1, a plurality of slits may be provided as described in Non Patent Literature 2.

It has been described that the trap rate (/one trapping structural member) of the bio-related substances in the trapping structural member is computed by [$\alpha$: (flow volume into trapping structural members)/(total flow volume)]×[$\beta$: bio-related substance trap rate in trapping structural members], and can be approximated by $\alpha$. It has also been described that, because the number of the required trapping structural members becomes smaller as the $\alpha$ increases, $\alpha$ can be increased to 0.001 by varying the slit width or the flow passageway width.

Figure 11:
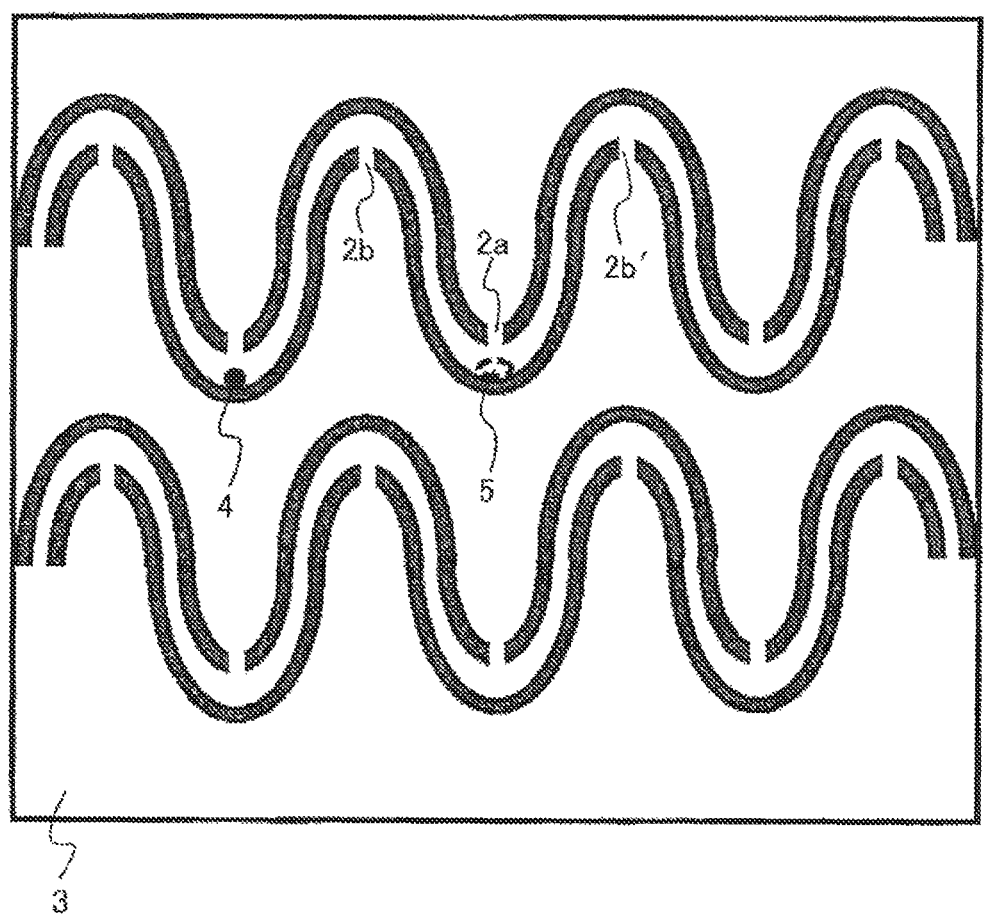
FIG. 11 is a schematic diagram of an example of the trapping structural member.

FIG. 11 is a schematic diagram of an example of the arrangement for making a one. All of the solution containing the bio-related substances 4 pass the slits of the trapping structural members, so that this example can be considered to represent a variation of the shape of FIG. 1 where the intervals between the trapping structural members are made zero. From an injection opening, not shown, disposed at the top of FIG. 11, the solution containing the bio-related substances 4, not shown, is injected, sent through the flow passageway 3, and discharged via a discharge opening, not shown, located at the bottom of FIG. 11. In this process, as the solution containing the bio-related substances 4, not shown, passes through a slit 2a and flows out via slit 2b or 2b', the bio-related substances 4 are trapped in the dead water region 5 with a certain probability. The dead water region 5 is a region where there is no flow or a region where the flow, if any, is whirling and that has nothing to do with the canalization of flow volume. The bio-related substances 4 that have passed the slit 2 are trapped in the dead water region 5 with a certain probability by diffusion, inertial force, or their motility. Thus, the bio-related substances 4 are not trapped by a slit (hole) of a smaller size, as in the case of a filter. It is also possible to collect the bio-related substances 4 trapped in the dead water region. Specifically, when the sending of the solution is stopped, the bio-related substances 4 trapped in the dead water region deviate from the dead water region 5 due to the diffusion or motility of the substance. The solution is then sent in the opposite direction. Namely, the collected fluid is injected via the injection opening which is not shown, at the bottom of FIG. 1, and caused to pass the slit 2b or 2b' via the flow passageway 3 and flow out via the slit 2a. Thus, the collected fluid is discharged via the discharge opening, not shown, at the top of FIG. 11, together with the bio-related substances 4. Because FIG. 11 is a vertically symmetric shape, when the collected fluid is injected via the injection opening, not shown, at the bottom of FIG. 11, the dead water region 5 that was initially present is eliminated, and instead a dead water region is formed at the top of the slits 2b and 2b' in the figure. Thus, in the case of the sending of solution in the opposite direction, there is also the possibility that the substance is trapped before reaching the unillustrated discharge opening. In that case, a procedure of stopping the sending of solution again so as to allow the bio-related substances 4 to deviate from the dead water region by diffusion or motility of the substance and then sending the solution may be repeated, whereby the bio-related substances 4 can be eventually collected. Alternatively, the bio-related substance may be collected via the discharge opening by repeating only the sending of solution and the stopping of the sending without changing the solution sending direction. When the bio-related substances 4 can be collected, its nucleic acid may be extracted so that an analysis, such as gene analysis by PCR, can be performed.

Figure 12:
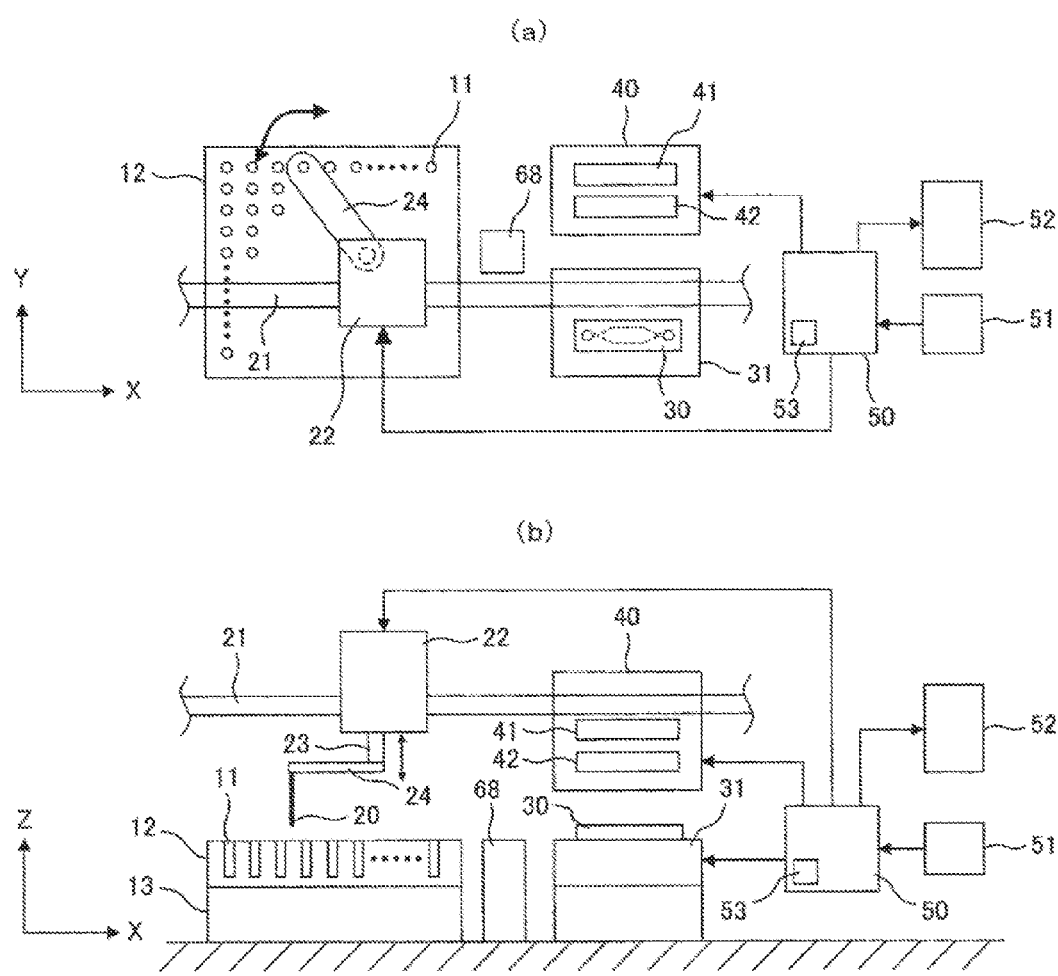
FIG. 12 is a schematic diagram of an example of an analysis device.

FIG. 12 is a schematic diagram of an example of an analysis device (bacterial analysis device) according to the present invention. FIG. 12(a) is a schematic plan view of the device, and FIG. 12(b) is a schematic front view. The following description will be made with reference to X, Y, and Z axes set as shown.

The analysis device according to the present embodiment is provided with a reagent rack base 13 on which a reagent rack 12 for holding a plurality of reagent containers 11 is placed; a flow cell stage 31 movable while holding one or a plurality of flow cells 30; a sampling nozzle 20 capable of suctioning or discharging a liquid via its tip; a nozzle drive mechanism for driving the sampling nozzle 20 to a desired three-dimensional position; a washing tank 68 for washing the sampling nozzle 20; and a detection unit 40 for analyzing a reaction with the bio-related substance trapped in the flow cell 30 or the bio-related substance itself by reagent injection. Suctioning or discharging of the reagent via the sampling nozzle 20 or its washing and the like are performed by a solution sending system, which is not shown. The solution sending system will be described in detail with reference to FIG. 13.

The various units of the analysis device are under the control of a control/computation unit 50. The control/computation unit 50 controls and continuously operates the analysis device in accordance with a program set in the control/computation unit 50 via a input unit 51. A memory in the control/computation unit 50 stores information about, e.g., an analysis procedure; coordinate positions of the plurality of reagent containers 11 placed in the reagent rack 12 and the washing tank 68; the types of reagents in the respective reagent containers; the coordinate position of the injection port for injection of the reagents or washing fluid into the flow cells 30; and a procedure for processing the result of detection by the detection unit 40. The control/computation unit 50, with reference to the information stored in the memory, controls the various units of the device and executes an analysis in accordance with the analysis program.

The sampling nozzle 20 is, e.g., a hollow nozzle with a tip portion measuring 1 mm in external diameter, 0.5 mm in internal diameter, and 150 mm in length and made from metal material, such as SUS. The sampling nozzle 20 is connected to the solution sending system, which will be described later. The sampling nozzle 20 can suction a required amount of reagent from the desired one of the reagent containers 11 placed in the reagent rack 12 into the tip portion, and discharges the reagent into the flow cell 30 or the like. The material and structure of the sampling nozzle 20 are adapted for fluid level sensing. Fluid level sensing is performed, for example, by a fluid level sensing unit 53 of the control/computation unit 50 using a known system whereby the fluid level is sensed based on a capacitance change caused when the tip of the metal sampling nozzle 20 contacts a conductive region such as the fluid level. The fluid level sensing unit 53 outputs a fluid level sense signal that is utilized for subsequent device control.

The nozzle drive mechanism includes a guide rail 21; a linear movement unit 22 that moves linearly in an X-axis direction along the guide rail 21; and an arm 24 rotatable about a rotating shaft 23 of the linear movement unit 22. The sampling nozzle 20 is affixed to the arm 24 on the opposite side from the rotating shaft 23. The linear movement unit 22 includes, e.g., a pinion meshed with a rack provided on the guide rail 21, so that the linear movement unit 22 can be moved to a desired position in the X-axis direction by rotating the pinion with a stepping motor. The rotating shaft 23 is also rotatable by a stepping motor in an XY plane. The rotating shaft 23 can also be moved vertically along the Z-axis direction so as to position the tip of the sampling nozzle 20 at a desired Z-axis position. Based on a combination of the linear movement in the X-axis direction, the rotation movement about the rotating shaft 23, and the vertical movement in the Z-axis direction by the nozzle drive mechanism, the sampling nozzle 20 can access any of the reagent containers 11 placed in the reagent rack 12, the washing tank 68, or the injection port of the flow cells as will be described below.

The detection unit 40 includes a light source 41 that irradiates the flow cells, and an imaging device 42, such as a CCD, that detects Raman light produced by the bio-related substance present in the flow cell 30 upon optical irradiation from the light source, via optical components such as a diffraction lattice that scatters the Raman light, a mirror, a filter, a slit, and a confocal detection hole. The detection unit 40 may also be configured for bright field, dark field, phase difference, differential interference, fluorescence, or light emission by selecting the optical system, and is thus not limited to Raman observation.

The flow cell 30 is movable by the flow cell stage 31 in XY-axes directions. As illustrated, the flow cell 30, when subjected to operations via the sampling nozzle 20, such as the injection of reagent or washing, is positioned at a location displaced from under the detection unit 40. During detection using the detection unit 40, the flow cell 30 is moved by the flow cell stage 31 to a position under the detection unit 40. A display unit 52 displays various information, such as input information input from the input unit 51; analysis process information such as images taken by the detection unit 40; current device state or parameter information; information about the completed analysis steps; and an analysis result.

It is also possible to place the detection unit 40 under the flow cell 30, as in a general biological microscope. In this arrangement, the detection unit 40 can perform detection while a reagent is discharged from the sampling nozzle 20 over the flow cell 30. Similarly, the flow cell 30 may also be placed at an angle or vertically, as well as horizontally as illustrated in FIG. 12. For example, the flow cell 30 may be vertically placed so that detection can be performed by the detection unit 40 which is vertically placed while the solution is being sent. By sending the solution from the bottom to the top of the vertically placed flow cell 30, removal of air bubbles in the flow cell 30 can be facilitated. When the specific weight of a bacterium is smaller than the specific weight of reagent, buoyancy may be utilized for trapping; when greater, gravity may be utilized for trapping.

Figure 13:
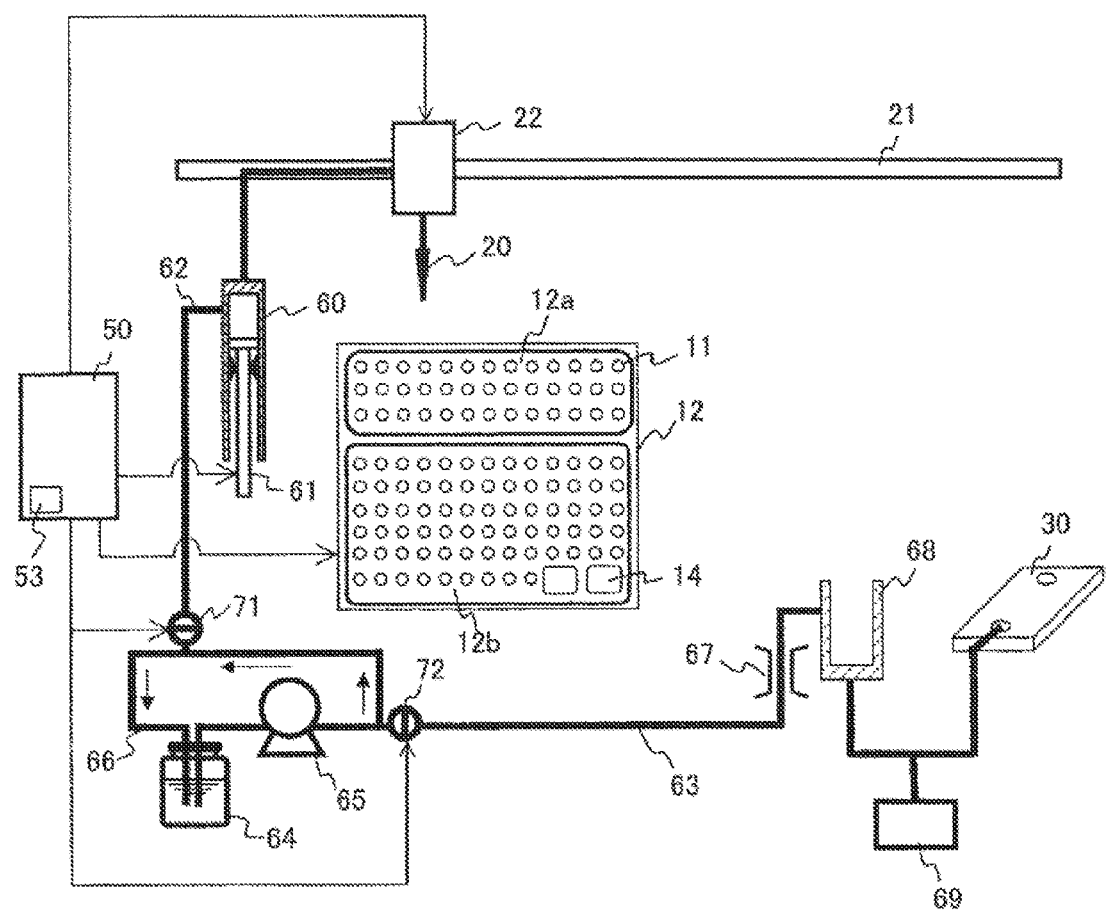
FIG. 13 is a schematic diagram of an example of the analysis device.

FIG. 13 is a schematic diagram of an example of the solution sending system incorporated into the analysis device of the present embodiment. The solution sending system performs the suctioning or discharging of reagent via the tip of the sampling nozzle 20, and the washing of the sampling nozzle 20. The solution sending system of the present embodiment includes a microsyringe 60 for weighing the reagent from the tip of the sampling nozzle 20 for suctioning or discharging; and a first flow passageway 62 and a second flow passageway 63 for supplying a washing fluid to the sampling nozzle 20 and the washing tank 68, respectively. According to the present embodiment, the washing fluid accumulated in the washing fluid tank 64 is suctioned up by a continuously driven pump 65 and returned back to the washing fluid tank 64 via the washing fluid circulation flow passageway 66. Namely, the washing fluid is constantly circulated by the pump 65 through the washing fluid circulation flow passageway 66 in the arrow direction. The first flow passageway 62 of which one end is connected via a first electromagnetic valve 71 to the washing fluid circulation flow passageway 66 has its other end being communicated with the inside of the sampling nozzle 20 via the microsyringe 60. Similarly, the second flow passageway 63 of which one end is connected via a second electromagnetic valve 72 to the washing fluid circulation flow passageway 66 has its other end being opened in a side wall the washing tank 68. As the washing fluid, pure water is used, for example.

When the portion of the sampling nozzle 20 is moved into the washing tank 68 by the nozzle drive mechanism and, in that state, if only the first electromagnetic valve 71 is placed in open state, the washing fluid pressure-fed from the pump 65 is ejected via the sampling nozzle 20 into the washing tank 68, whereby the inside of the sampling nozzle 20 can be washed. During the washing, the plunger 61 of the microsyringe 60 may or may not be moved. If only the second electromagnetic valve 72 is placed in open state, the washing fluid is ejected from an inner wall of the washing tank 68, whereby the outside of the sampling nozzle 20 can be washed. Further, when the first electromagnetic valve 71 and the second electromagnetic valve 72 are simultaneously placed in open state, both the inside and outside of the sampling nozzle 20 can be simultaneously washed within the washing tank 68. The opening and closing of the first electromagnetic valve 71 and second electromagnetic valve 72 are controlled by the control/computation unit 50.

The ratio of the washing fluid supplied to the sampling nozzle 20 via the first flow passageway 62 to the washing fluid supplied to the washing tank 68 via the second flow passageway 63 is set by a flow volume adjustment aperture 67 disposed at a location near the washing tank 68 for the second flow passageway 63. The washing fluid with which the sampling nozzle 20 has been washed is accumulated in a waste fluid tank 69. The washing fluid accumulated in the washing tank 68 can be accumulated in the waste fluid tank 69 using a waste fluid discharge pump, which is not shown. The washing fluid can also be sent from the washing fluid tank 64 by opening the second electromagnetic valve 72 and drawing with a waste fluid discharge pump with the washing tank 68 sealed. By performing a similar operation with the washing fluid tank 64 emptied, and further by opening the first electromagnetic valve 71, liquids in the first flow passageway 62, the second flow passageway 63, and the washing fluid circulation flow passageway 66 can also be removed. When the pump 65, the second electromagnetic valve 72, and the piping are not correctly connected, the washing fluid cannot leave the washing tank 68 and therefore the sampling nozzle 20 cannot be washed. In this case, failure can be sensed by the absence of activation of the fluid level sense function of the nozzle. By performing the wash operation, the washing fluid in the washing fluid tank 64 is consumed. The washing fluid tank 64 is installed with a fluid level sensor so that, when the washing fluid in the washing fluid tank 64 is decreased, the washing fluid tank 64 can be replenished with washing fluid from a separately installed washing fluid replenish tank, which is not shown. Thus, in the solution sending system according to the present embodiment, large amounts of washing fluid can be supplied to the inside or outside, or both the inside and outside, of the sampling nozzle in a short time using pumps, whereby the reagent attached to the sampling nozzle after use cat be washed sufficiently in a short time. Accordingly, contamination of the reagent can be avoided and analysis accuracy can be increased. Further, the washing time can be decreased so that the throughput of analysis can be increased.

The reagent rack 12 is provided with a temperature sensor and a temperature adjustment unit, such as the Peltier element, so as to maintain a constant temperature of the reagents held in the reagent containers 11. For example, a group of reagents held in a first region 12a of the reagent rack is maintained at room temperature, while a group of reagents held in a second region 12b is maintained at 4° C. The temperature control of the reagent rack 12 may also be performed from the control/computation unit 50. Depending on the type of reagent, it may be desirable to mix a plurality of reagents immediately before use and then supplying the mixture to the flow cell. Thus, the reagent rack 12 is provided with a pre-mix container 14 for use in preparing a reagent mixture. When using a reagent mixture, each reagent suctioned from separate reagent containers 11 by the sampling nozzle 20 is discharged into the pre-mix container 14, and the reagent mixture mixed and prepared in the pre-mix container 14 is again suctioned by the sampling nozzle 20 and supplied to the flow cell 30.

FIG. 14 is a schematic diagram of an example of the flow cell FIG. 14(a) is a perspective view of the flow cell, and FIG. 14(b) is a cross sectional view taken along line X-X' of FIG. 14(a). In this example, the flow cell includes injection ports 32, discharge ports 33, and flow passageways 34 in which fluid flows. The flow passageways 34 are formed between an upper substrate 36 and a lower substrate 37, and the flow cell 30 is designed such that the bio-related substances 4 can be trapped by the trapping structural members 1 illustrated in FIG. 1. The flow passageways 34 function as a flow passageway for supplying the reagent for bacterial analysis or washing fluid, and also as a reaction chamber where a reaction takes place. For example, with respect to a bacterium trapped in the flow cell 30, a Gram stain reaction may be caused so as to observe, using the detection unit 40, a Gram-positive bacterium being stained purple or a Gram-negative bacterium being stained pink. In order to ensure a space for the flow passageways 34, a spacer 38 is placed between the upper substrate 36 and the lower substrate 37. The spacer 38 may be integral with the upper substrate 36 or the lower substrate 37 so that the flow cell 30 having the trapping structural members of FIG. 1 or FIG. 11 can be fabricated. The reagent is injected via the injection ports 32 and discharged via the discharge ports 33. The spacer may have a thickness of 50 to 100 µm, a flow passageway width of 1 to 30 mm, and a flow passageway length of 75 to 100 mm but are not limited to these numerical values. The upper substrate 36 on the side facing the detection unit 40 may comprise material that transmits excitation light and fluorescence, such as glass, quartz, sapphire or PDMS, or a resin such as acrylic resin or cycloolefin polymer. In the example of FIG. 14, the flow cell 30 has three flow passageways; however, the number of the flow passageways is not limited to three. When the number of the flow passageways is large, a number of reactions may be caused at once, whereby high-throughput analysis may be performed. During Raman analysis, the flow cell 30 is controlled to a predetermined temperature by a temperature control unit provided for the flow cell stage 31.

Next, procedure for installing the reagent rack 12 on the reagent rack base 13 of the analysis device and performing analysis by supplying reagent to the flow cell, with the flow cell 30 installed on the flow cell stage 31, will be described.

(1) Washing of Sampling Nozzle

Figure 15:
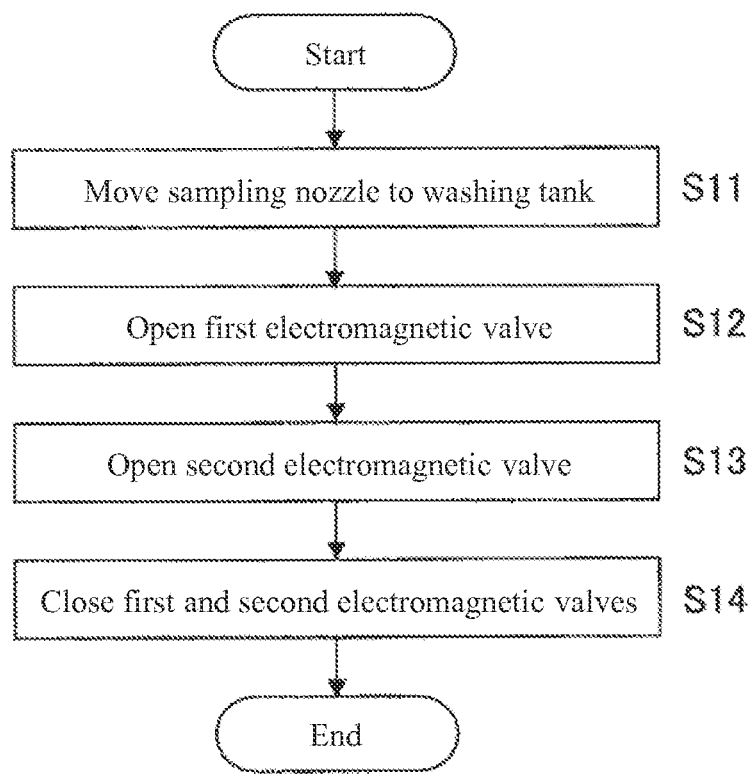
FIG. 15 is a flowchart of an example of a control procedure for washing a sampling nozzle.
Figure 16:
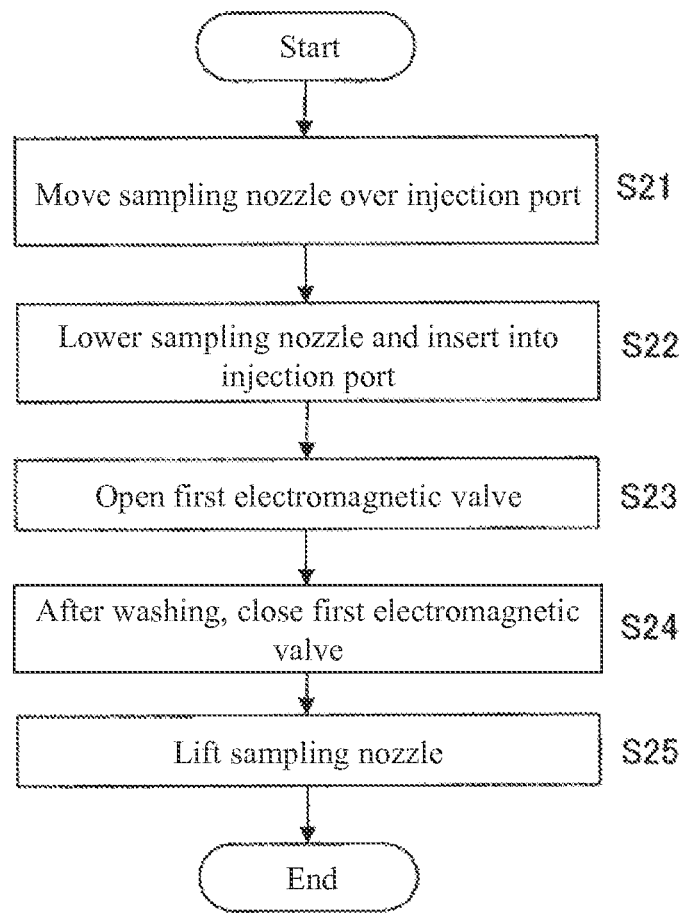
FIG. 16 is a flowchart of an example of a control procedure for washing the inside of the flow cell.

First, the sampling nozzle 20 is washed. A control procedure for this purpose by the control/computation unit 50 is shown in FIG. 15. The control/computation unit 50 first controls the nozzle drive mechanism to move the sampling nozzle 20 to the washing tank 68 (S11). The control/computation unit 50 then controls the first electromagnetic valve 71 connected to the washing fluid circulation flow passageway 66 in which washing fluid is being circulated by the pump 65, placing the valve in open state (S12). The plunger 61 of the microsyringe 60 may or may not be moved during the washing. In this state, the washing fluid pressure-fed from the pump 65 enters the microsyringe 60 via the first electromagnetic valve 71 and the first flow passageway 62, and is ejected as is into the washing tank 68 from the nozzle tip via the sampling nozzle 20. In this state, the nozzle inside is washed. As the washing fluid, pure water may be used.

Next, the control/computation unit 50 controls the second electromagnetic valve 72 connected to the washing fluid circulation flow passageway 66, placing the valve in open state (S13). Then, the washing fluid pressure-fed from the pump 65 passes through the second electromagnetic valve 72 and the second flow passageway 63 and is ejected into the washing tank 68 via the inner wall of the washing tank, thereby washing the outside of the sampling nozzle 20 positioned in the washing tank 68. Thus, the inside and outside of the sampling nozzle 20 are washed as illustrated in FIG. 5. After the washing is completed, the control/computation unit 50 closes the first electromagnetic valve 71 and the second electromagnetic valve 72 (S14).

Instead of opening the first electromagnetic valve 71 first and then opening the second electromagnetic valve 72, the first electromagnetic valve 71 and the second electromagnetic valve 72 may be simultaneously opened. In this case, the washing of the inside and outside of the sampling nozzle is simultaneously performed. The order of washing may be the nozzle outside first followed by the nozzle inside.

In either case, when the first electromagnetic valve 71 is closed after the washing of the sampling nozzle inside is completed, the portions from the first flow passageway 62 connected o the washing fluid circulation flow passageway 66 to the microsyringe 60 and the tip of the sampling nozzle 20 are filled with washing fluid.

By the washing method according to the present embodiment, a large amount of washing fluid can be supplied to the inside or outside, or both the inside and outside, of the sampling nozzle in a short time, whereby the washing time can be reduced and the throughput of analysis can be increased.

(2) Washing of Flow Cell

Next, the inside of the flow cell 30 is washed. A control procedure for this purpose by the control/computation unit 50 is shown by a flowchart of FIG. 16.

The control/computation unit 50 controls the nozzle drive mechanism to move the sampling nozzle 20 to a position over the injection port 32 of the flow cell 30 (S21). Then, the sampling nozzle is lowered and the nozzle tip is inserted into the injection port (S22). The control/computation unit then opens the first electromagnetic valve 71 (S23). At this time, the plunger 61 of the microsyringe 60 may be affixed or moved. As a result, the washing fluid pressure-fed from the pump 65 passes through the first electromagnetic valve 71 and the first flow passageway 62 and enters the microsyringe 60, and further passes through the injection port 32 from the tip of the sampling nozzle 20 and flows into the flow passageway 34 of the flow cell 30, thus washing the flow cell. The washing fluid with which the flow passageway of the flow cell has been washed is stored in the waste fluid tank 69. After the washing of the flow cell is completed by opening the first electromagnetic valve 71 for a preset time, the control/computation unit 50 closes the first electromagnetic valve 71 (S24). Thereafter, the control/computation unit 50 lifts the sampling nozzle 20 away from the injection ports 32 by controlling the nozzle drive mechanism (S25). At this time, the control/computation unit 50, instead of commanding the nozzle drive mechanism to lift the sampling nozzle immediately after closing the first electromagnetic valve 71, commands the lifting of the sampling nozzle after waiting for a predetermined time to allow the washing fluid pressure in the flow cell to stabilize. This will be described later with reference to the injection of reagent into the flow cell.

(3) Suctioning of Reagent from Reagent Container

Figure 17:
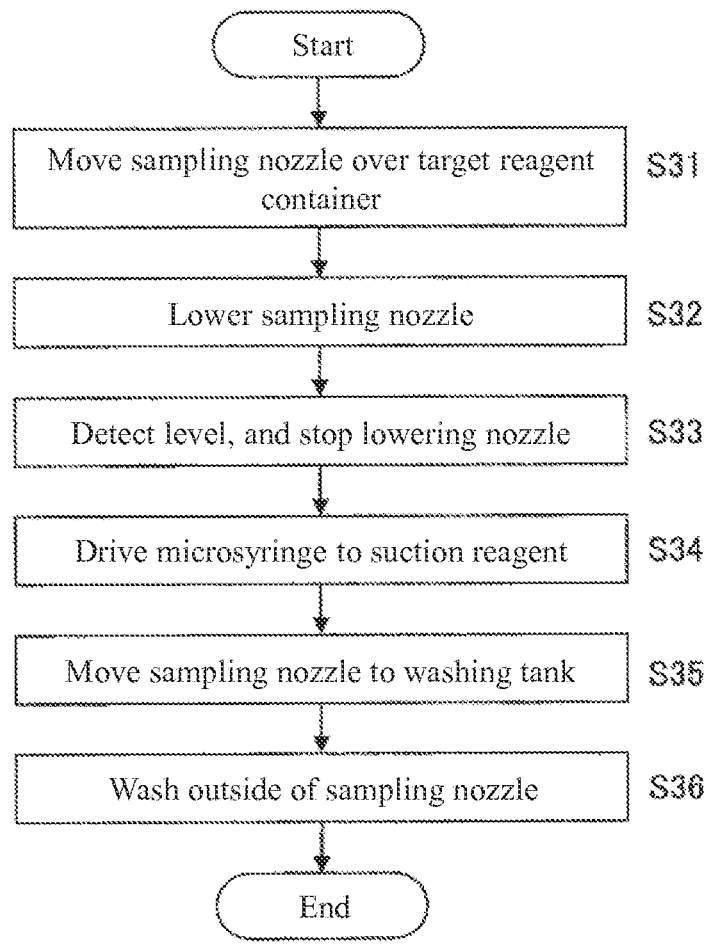
FIG. 17 is a flowchart of an example of a procedure for suctioning a reagent from a reagent container.

With reference to a flowchart of FIG. 17, a procedure for suctioning reagent from the reagent container 11 at a predetermined position in the reagent rack 12 using the sampling nozzle 20 will be described, assuming that the reagent is a bacteria-containing solution.

The control/computation unit 50, in accordance with a programmed procedure, determines the type and suctioning amount of the reagent to be suctioned. The control/computation unit 50 then determines the position to which the sampling nozzle is to be moved with reference to the information about the correspondence relationship between the reagent container position and the reagent type stored in the memory. Then, the control/computation unit 50 controls the nozzle drive mechanism to move the sampling nozzle 20 to a position over the reagent container containing the target reagent (S31). The sampling nozzle is then lowered and the nozzle tip is inserted into the reagent container (S32). At this time, the reagent fluid level in the reagent container is sensed using the fluid level sense function of the fluid level sensing unit 53. When the reagent fluid level has been sensed, the sampling nozzle is further lowered by a certain distance and, in a state where the nozzle tip is inserted into the reagent solution by a predetermined depth, the sampling nozzle is stopped (S33). The control/computation unit 50 then drives the plunger 61 of the microsyringe 60 toward the suctioning side by a predetermined amount so as to suction and hold the determined amount of reagent in front of the washing fluid filled in the sampling nozzle 20 (S34).

Then, control/computation unit 50 controls the nozzle drive mechanism to drive the sampling nozzle upward so as to remove the nozzle tip out of the reagent container and to further move the sampling nozzle to the washing tank 68 (S35). Thereafter, the control/computation unit 50 opens the second electromagnetic valve 72. As a result, the washing fluid is ejected from the inner wall surface of the washing tank 68, washing the reagent attached to the outside of the sampling nozzle 20 (S36). The reagent suctioned into the sampling nozzle remains and held inside the nozzle as is without being washed. After the washing of the outside of the sampling nozzle is completed, the control/computation unit 50 closes the second electromagnetic valve 72 and controls the nozzle drive mechanism so as to move the sampling nozzle 20 upward.

Because the tip of the sampling nozzle 20 inserted into the reagent is limited to a necessary minimum depth by the fluid level sense function, the amount of reagent that becomes attached to the outside of the sampling nozzle 20 and that is washed away in the washing tank 68 can be suppressed to a minimum at all times. Another advantage of performing the reagent fluid level sensing is that the remaining amount of reagent can be known from the information about the shape of the reagent container and the fluid level height. Thus, the number of remaining bases that can be analyzed can be coupled, or the user can be informed of the timing for reagent replacement.

(4) Injection of Reagent into Flow Cell

Figure 18:
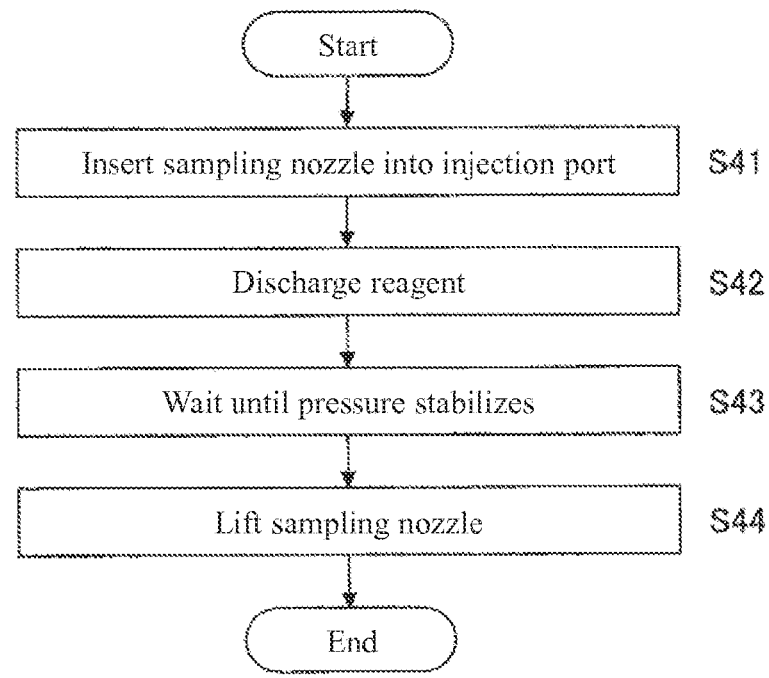
FIG. 18 is a flowchart of an example of a procedure for injecting the reagent into the flow cell.

With reference to a flowchart of FIG. 18, a procedure for injecting the reagent suctioned and held in the tip of the sampling nozzle 20 into the flow cell 30 will be described.

First, the control/computation unit 50 controls the nozzle drive mechanism so as to move the sampling nozzle 20 to a position over the injection port 32 of the flow cell 30. Then, the sampling nozzle 20 is lowered and the nozzle tip is inserted into the injection port 32 (S41). The control/computation unit 50 then drives the plunger 61 of the microsyringe 60 in the discharge direction so as to cause the reagent suctioned in front of the washing fluid filled in the sampling nozzle 20 into the flow cell 30 via the injection port 32 (S42). In the flow cell 30, a number of the trapping structural members 1 illustrated in FIG. 1 are arranged, and the bacteria contained in the reagent are trapped in the trapping structural members as the solution is sent. After the driving of the plunger 61 is completed, the control/computation unit 50 waits until the pressure in the flow cell 30 is stabilized (S43), and then controls the nozzle drive mechanism to lift the sampling nozzle upward (S44).

Figure 19:
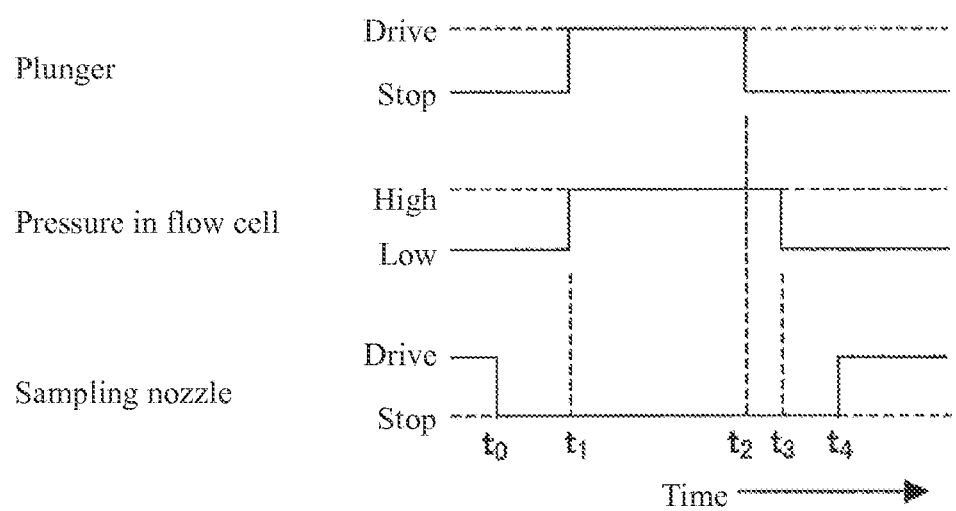
FIG. 19 illustrates the relationship between the timings of insertion or removal of the sampling nozzle into or from the injection port and driving of a microsyringe plunger and changes in the pressure in the flow cell.

FIG. 19 schematically illustrates the relationship between the timings of insertion or removal of the sampling nozzle into or from the injection port and the driving of the microsyringe plunger, and the change in pressure in the flow cell. The horizontal axis shows time. FIG. 19 indicates that the sampling nozzle 20 is inserted into the injection port 32 of the flow cell at time t0, and then lifted upward from the injection port 32 at time t4. The plunger 61 of the microsyringe 60 is driven from time t1 to t2 for discharging reagent.

The reagent is pressure-injected into the low-conductance flow passageway of the flow cell by driving the plunger 61 of the microsyringe 60. Thus, the pressure in the flow cell 30 is high immediately after the driving of the plunger 61 is stopped (time t2). Therefore, if the sampling nozzle 20 is pulled away from the injection port 32 immediately, the reagent may flow backward and spill out of the injection port 32. According to the present embodiment, the sampling nozzle 20 is separated from the injection port 32 and lifted upward after waiting for a time from the reagent injection operation end time t2 until the pressure in the flow cell 30 is stabilized. Namely, the time t4 at which the sampling nozzle 20 is lifted from the injection port 32 is set such that t4>t3. The wait time (t3–t2) until the pressure in the flow cell is stabilized is determined by, e.g., the viscosity of the injected reagent, the speed of injection, and the flow passageway resistance of the flow cell; typically, the wait time may be on the order of from 0.5 second to one second.

After the reagent is injected into the flow cell, the control/computation unit 50 controls the nozzle drive mechanism to move the sampling nozzle 20 to the washing tank 68. Then, the inside and outside of the sampling nozzle are washed in accordance with the procedure described with reference to (1) Washing of sampling nozzle, in preparation for the next operation.

In the reagent suctioning and reagent injection procedure according to the present embodiment, the amount of the reagent to be injected from the sampling probe into the flow cell is sufficient if the amount corresponds to the volume of the flow cell to which the volume corresponding to a dead space at the injection port 32 of the flow cell is added. It is estimated that the volume of the dead space will be not more than 5 μl. Thus, the amount of reagent that needs to be injected into the flow cell 30, namely, the amount of reagent that needs to be suctioned from the reagent container 11 into the sampling nozzle 20, is a least the volume of the flow cell and would be sufficient if a volume on the order of 5 μl to 10 μl at most is added to the volume of the flow cell. Thus, according o the present embodiment, the amount of reagent that is suctioned from the reagent container for injection into the flow cell is small, and the amount of reagent that becomes attached to the outside of the sampling nozzle 20 and then washed away is small. In other words, the amount of reagent used is small, resulting in less waste of reagent. Accordingly, the present embodiment makes it possible to effectively utilize expensive reagents.

Further, according to the present embodiment, the suctioning of reagent and the sending of solution to the flow cell are implemented by the sampling nozzle, whereby the solution sending time can be decreased compared with a system using tubes and a switching valve. Also, reagent carry-over is very little, enabling a purer reagent to be supplied to the flow cell.

(5) Detection

Figure 20:
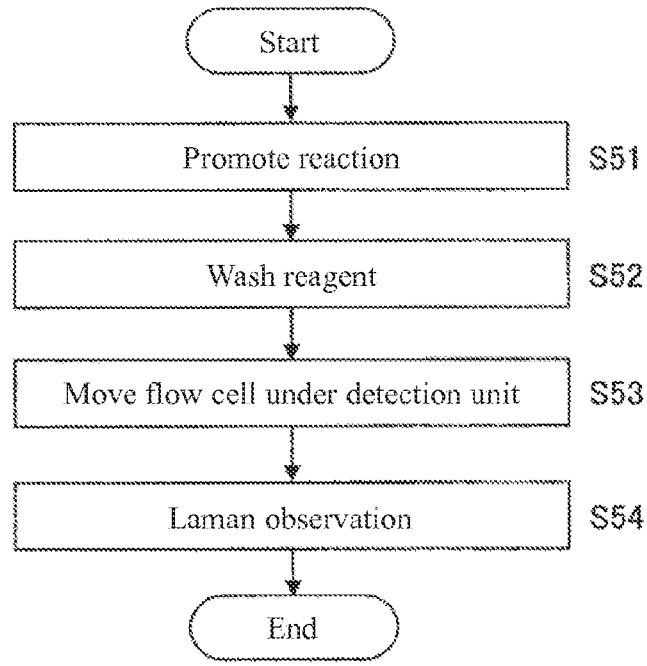
FIG. 20 is a flowchart of an example of a detection procedure.

A detection procedure will he described with reference to a flowchart of FIG. 20.

After the reagent is injected into the flow cell and bacteria are trapped, the temperature of the flow cell 30 is controlled to an optimum temperature (S51). As needed, the control/computation unit 50 may execute the process described with reference to (2) Washing of flow cell, or the process described with reference to (3) Suctioning of reagent from reagent container and (4) Injection of reagent into flow cell with respect to the washing fluid (reagent) placed in the reagent rack 12, so as to wash the inside of the cell (S52). Then, the control/computation unit 50 controls the driving of the flow cell stage 31 to move the flow cell 30 to a position under the detection unit 40 (S53).

When a transparent bio-related substance, such as a cell or a bacterium, is confirmed, a phase-contrast microscope is generally used. When a bacterium is observed under the phase-contrast microscope, a relatively strong light called "halo" is produced around the bacterium. Although the size of bacteria is small at several microns, the size of halo increases with increasing distance from the focal point of the microscope, and may reach several dozen microns. Thus, by finding the halo when trying to identify the trapping structural members in which bacteria are trapped, it can be known that a bacterium is present at the center of the halo, and that displacement from the focal point of the microscope, as known by the size of the halo, can be corrected. Then, the control/computation unit 50 causes the detection unit 40 to emit light so as to detect Raman light emitted from the bacteria in the flow cell 30 (S54). An analysis of the Raman light provides insights into the vibration or rotating motion of atoms or molecules, which insights can be applied for Gram determination of bacterial species, bacterial species identification, or bacterial strain determination. It is also possible, for example, to make Gram determination or antibiotic susceptibility determination for a bacterium by sending a solution of a Gram determination reagent or antibiotic susceptibility test reagent to the bacteria trapped in the flow cell.

(6) Collection

Figure 21:
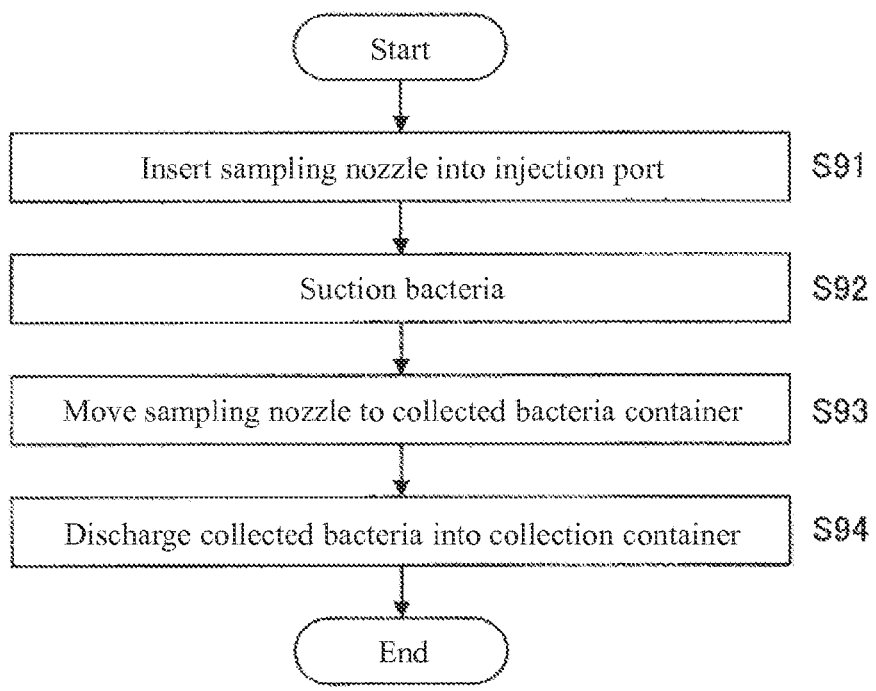
FIG. 21 is a flowchart of an example of a collection procedure.

A procedure for collecting the analyzed bacteria will be described with reference to a flowchart of FIG. 21.

The bacteria collection is performed at the end of the detection (5) in the flow cell. The control/computation unit 50 controls the nozzle drive mechanism to insert the sampling nozzle 20 into the injection port 32 of the flow cell 30 in which reaction has ended (S91). Then, the plunger 61 of the microsyringe 60 is driven to the suctioning side and the bacteria in the flow cell 30 are suctioned (S92). Alternatively, while a solution is sent toward the sampling nozzle 20 using a pump not shown on the discharge side of the flow cell, the plunger 61 of the microsyringe 60 may be suctioned at the same solution sending speed. The control/computation unit 50 then controls the nozzle drive mechanism to move the sampling nozzle 20 to a reagent collection container prepared in the reagent rack 12 (S93), and the suctioned bacteria are discharged into the container for collection (S94). Obviously, the bacteria collection container is prepared for each sample. Alternatively, the bio-related substances may be collected from the discharge opening by repeating only the sending of solution and the stopping of the sending of solution without changing the solution sending direction. After the collection of bacteria is completed, the control/computation unit 50 controls the nozzle drive mechanism to move the sampling nozzle 20 to the washing tank 68 where the inside and outside of the sampling nozzle 20 are washed in preparation for the next operation. The reagent collected in the reagent collection container may be used similarly to the reagent in the normal reagent containers. The collected bacteria may be subjected to, e.g., extraction of nucleic acid for analysis, such as bacteria identification by nucleic acid amplification by PCR and the like.

The solution sending system of the embodiment includes the washing fluid circulation flow passageway 66 provided with the pump 65. The washing fluid is supplied from the washing fluid circulation flow passageway 66 to the first flow passageway 62 or the second flow passageway 63 via the electromagnetic valves 71 and 72. However, the washing fluid circulation flow passageway may not necessarily be required.

In the foregoing, the embodiments in which e present invention is applied to bacterial analysis have been described. However, the present invention may be applied not only to bacterial analysis but also to methods in general where a solution containing the bio-related substances, such as cells or bacteria, is sent to a device where the substances are placed at single and independent positions for analysis. The bio-related substance refers to a substance such as a small molecule, protein, antigen antibody, hormone, a bacterium, or a cell, or a bound substance of such substance and an artificial substance such as a fine particle. As long as there is the device in which the bio-related substances are trapped, that device may be carried by hand and installed in a Raman microscope or the like for analysis, or subjected to automatic analysis using the solution sending system disclosed by the present invention.

The present invention is not limited to the foregoing embodiments and may include various modifications. The foregoing embodiments have been described for the purpose of aiding an understanding of the present invention and are not limited to those having all of the described configurations. A part of the configuration of a certain embodiment may be substituted by the configuration of another embodiment, or the configuration of the other embodiment may be added to the configuration of the certain embodiment. With respect to a part of the configuration of each embodiment, addition, deletion, or substitution of another configuration may be possible.

The above-described configurations, functions, processing units, processing means and the like may be partly or entirely realized by hardware, such as by designing an integrated circuit. The above-described configurations, functions and the like may be realized by software, such as a program interpreted and executed by a processor for realizing the functions. Information for realizing the functions, such as programs, tables, or files, may be placed in a recording device such as a memory, a hard disk, or an SSD, or a recording medium such as an IC card, an SD card, or a DVD.

Figure 22:
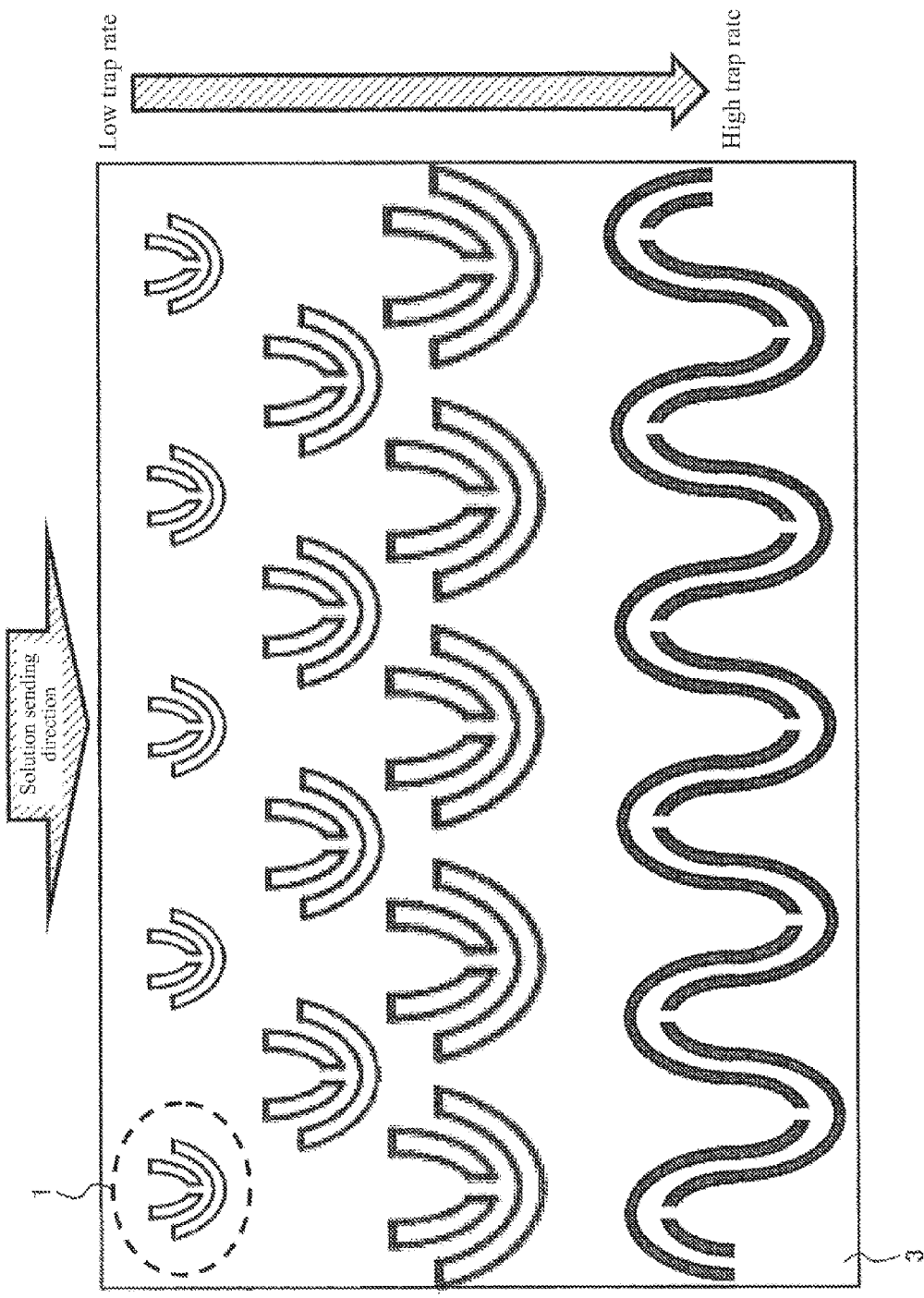
FIG. 22 is a schematic diagram of an example of the structural members with varied trap rates in each column.
Figure 23:
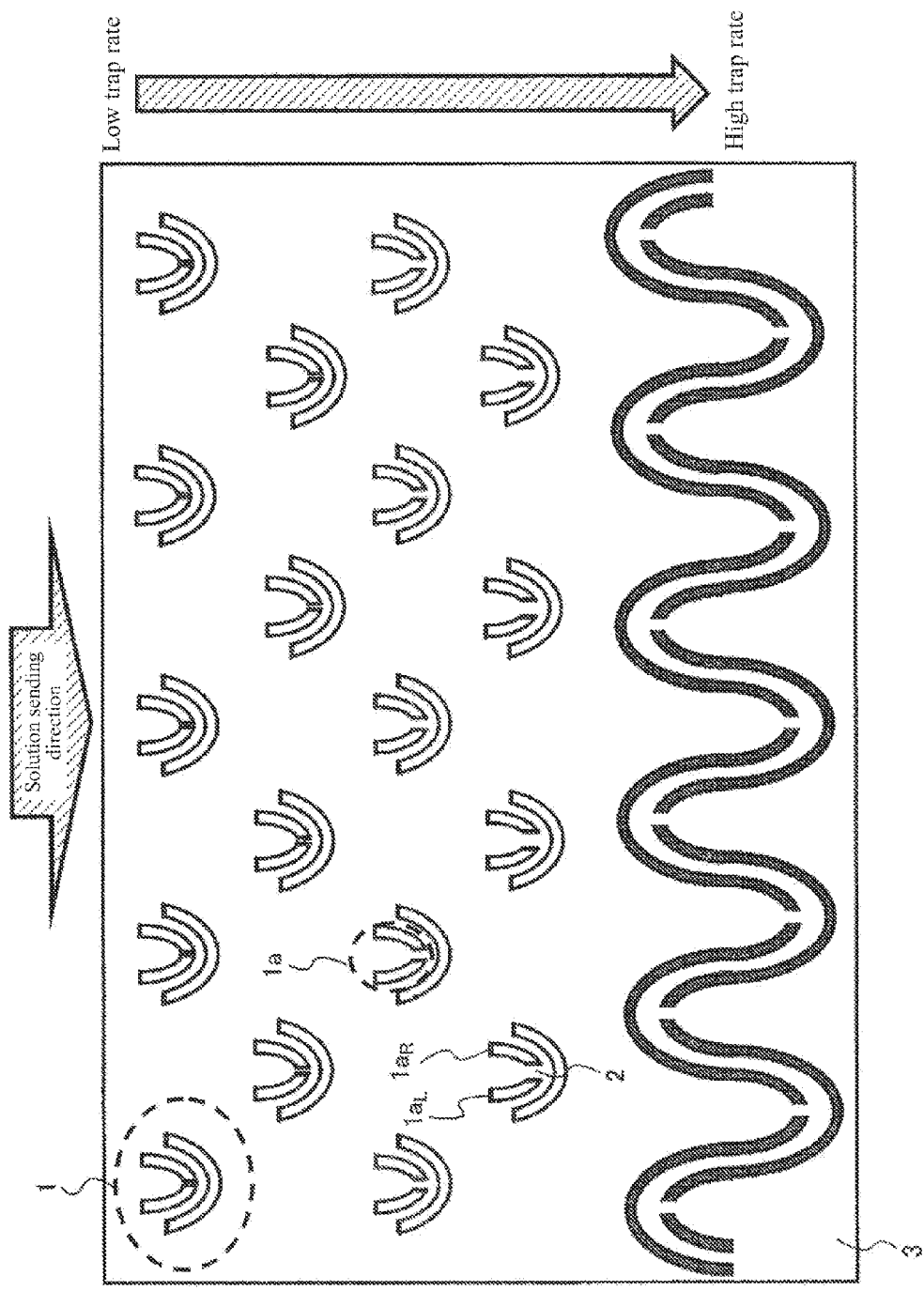
FIG. 23 is a schematic diagram of an example of the structural members with varied trap rates in each column.
Figure 24:
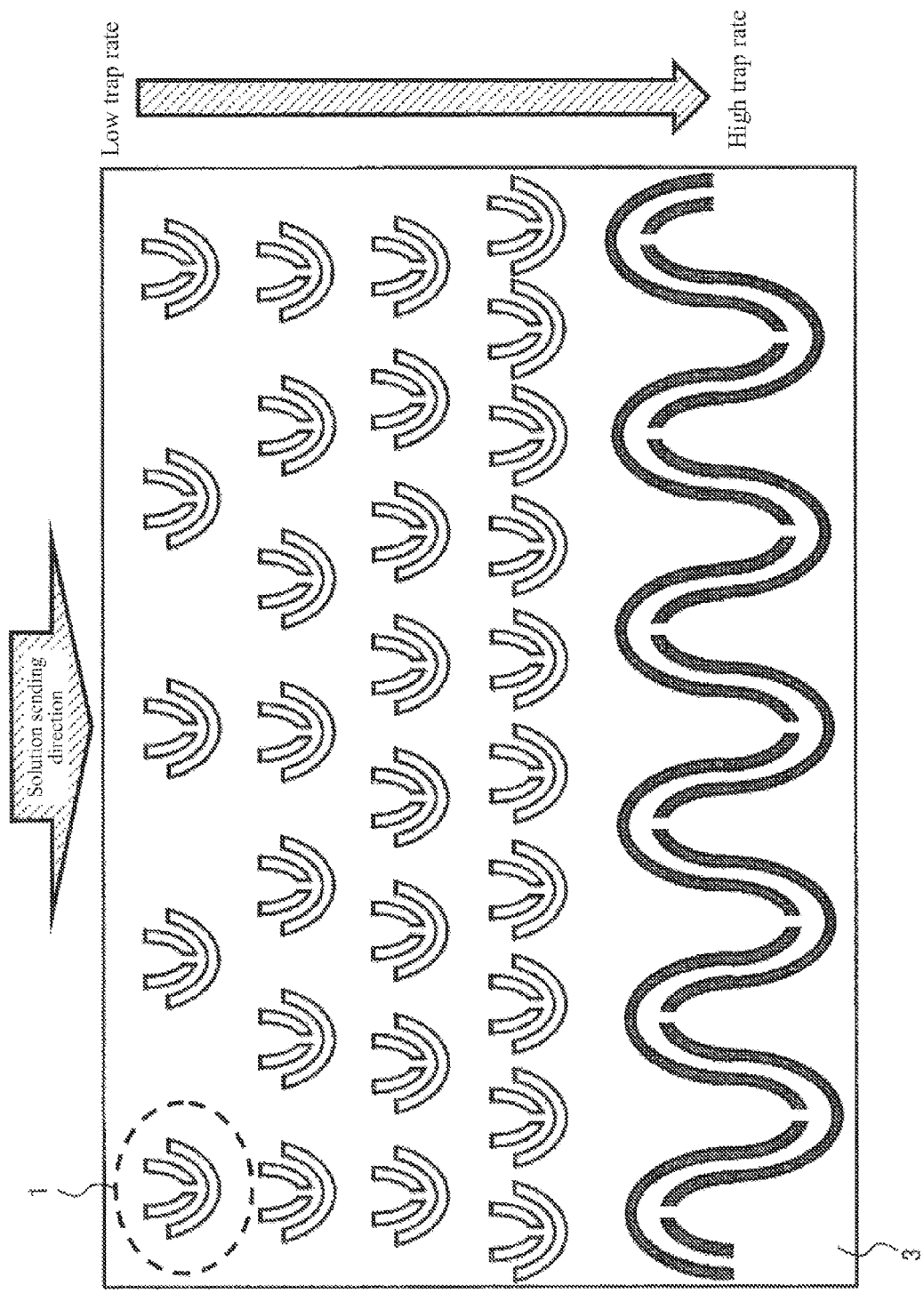
FIG. 24 is a schematic diagram of an example of the structural members with varied trap rates in each column.

In the following, various modification examples will be described. First, a method for achieving the same trap rate using a smaller number of columns of the trapping structural members than in FIG. 6 will be disclosed. in FIG. 6, when the Trap rate (/width) is 0.001, it has been described that the number of the trapping structural members that need to be placed in the solution sending direction (the x-direction) is 3000 for trapping 95%, 4700 for trapping 99%, or 7000 for trapping 99.9%. Because the trap rate in each column is the same, the Trap rate is computed by $1-[1-\{Traprate(/width)\}]^{\#Trap(x)/(/Channellength)}$. In this case, when the #Bacteria, which is the number of bacteria prior to solution sending to the trapping structural members, is 1000 and the Trap rate (/width) is 0.001, the number of bacteria trapped in the trapping structural members of the first column, or #Trapped bacteria (1st column), is one ($=1000\times\{1-(1-0.001)^1\}$); the number of bacteria trapped in the trapping structural members of the second column, or #Trapped bacteria (2nd column), is 0.999 [$=1000\times\{1-(1-0.001)^2\}$]; the number of bacteria trapped in the trapping structural members of the third column, or #Trapped bacteria (3rd column), is 0.998001 [$=1000\times\{1-(1-0.001)^3\}$]; and the number keeps decreasing. If the computation is continued, the number of bacteria trapped, or #Trapped bacteria, is, for example: 0.90569 for the 100th column; 0.779 for the 250th column; 0.60698 for the 500th column; 0.36806 for the 1000th column; 0.135335 for the 2000th column; 0.049762 for the 3000th column; 0.018297 for the 4000th column; 0.00672 for the 5000th column; 0.002473 for the 6000th column; and 0.0009 for the 7000th column, and the number keeps decreasing. Therefore, the number of bacteria trapped for each 1000 columns is decreased from 632 for the first to 1000th columns; 233 for the 1000th to 2000th columns; 85 for the 2000th to 3000th columns; 11 for the 3000th to 4000th columns; four for the 5000th to 6000th columns; and to two for the 6000th to 7000th columns. If the same trap rate (99.9%) can be achieved with a number of columns of the trapping structural members smaller than 7000, the detection region would become narrower and the detection time would be reduced. For this purpose, the same number of bacteria may be trapped in each column, Which can be achieved by varying the trap rate in each column. Preferably, the number of bacteria trapped in each column is, as described with reference to FIG. 7, not more than one so that a plurality of bacteria will not be trapped in the same trapping structural member. Thus, in the following, a case where one bacterium is trapped in each column will be described. When the number of bacteria before solution sending to the trapping structural members, or the #Bacteria, is 1000 and the Trap rate (/width) is 0.001, the number of bacteria trapped in the trapping structural members of the first column, or #Trapped bacteria (1st column), is one ($=1000\times\{1-(1-0.001)^1\}$); the number of bacteria trapped in the trapping structural members of the second column, or #Trapped bacteria (2nd column), is 0.999 [$=1000\times\{1-(1-0.001)^2\}$]; and the number keeps decreasing. In order to make the number of bacteria trapped in the trapping structural members of the second column, or #Trapped bacteria (2nd column), one as in the first column, the second column Trap rate (/width) may be increased from 0.001 to 0.0010010011 [$=1/(1000-(2-1))$]. Similarly, the third column may be 0.001002004 [$=1/(1000-(3-1))$]; the 100th column may be 0.00110987 [$=1/(1000-(100-1))$]; the 250th column may be 0.001331558 [$=1/(1000-(250-1))$]; the 500th column may be 0.001996008 [$1/(1000-(500-1))$]; the 750th column may be 0.0038984064 [$=1/(1000-(750-1))$]; the 900th column may be 0.00990099 [$=1/(1000-(900-1))$]; the 990th column may be 0.0909090 [$=1/(1000-(990-1))$]; the 999th column may be 0.5 [$=1/1000-(999-1))$]; and the 1000th column may be 1 [$=1/(1000-(1000-1))$]. When the 99.9% trap rate is acceptable, the trapping structural members of the 1000th column with the Trap rate (/width) of one are not required. Because the number of bacteria before solution sending to the trapping structural members, or #Bacteria, is 1000, and one bacterium is trapped by each column, all bacteria can be trapped if there are 1000 columns. This is 1/7 the number of columns in the case where the Trap rate (/width) is 0.001 in all of the columns (99.9% trap rate with 7000 columns). Thus, the Channel length shown in FIG. 7 may be decreased to 1/7, and also the detection time can be reduced. Such is the principle whereby the same trap rate can be achieved with a smaller number of columns of the trapping structural members than in FIG. 6. The Trap rate (/width) can be varied, as described with reference to FIGS. 2 to 4, which may be achieved by adjusting parameters such as the slit width, the flow passageway width, or flow velocity based on a flow simulation and the like. An example is illustrated in FIG. 22. In FIG. 22, the Trap rate (/width) is increased by increasing the size of the trapping structural members 1 toward the downstream side of the flow passageway 3, thus decreasing the amount of the solution passing between the trapping structural members. When the Trap rate (/width) is eventually made one, the flow volume that passes between the trapping structural members may be made zero, as in the structural members disclosed in FIG. 11. Because the arrangement is possible without changing the number of trapping structural members in each column, the intervals between the centers of the structural members can be made equal. However, this is not the case when the Trap rate (/width) is one, where all bacteria can be trapped. In FIG. 22, the trapping structural members are increased in size by increasing all dimensions of the trapping structural members 1. However, only a particular dimension of the trapping structural members 1, such as their thickness, may be increased. In FIG. 23, the Trap rate (/width) is increased by increasing the width of the slit 2 toward the downstream side of the flow passageway 3. Because the arrangement is possible without changing the number of trapping structural members in each column, the intervals between the centers of the structural members and their outer shape can be made equal. While there are no restrictions in the width of the slit 2, the width is preferably 1 to 50 µm. When it is desired to make the Trap rate (/width) one eventually, there is a limit if only the width of the slit 2 is increased. In this case, the purpose may be achieved by using in combination the structural members with the zero-flow volume between the trapping structural members, as in the structural members disclosed in FIG. 11. In FIG. 24, the Trap rate (/width) is increased in size by increasing the number of the trapping structural members 1 toward the downstream side of the flow passageway 3. When the Trap rate (/width) is eventually made one, it is also possible to make the flow volume passing between the trapping structural members zero, as in the structural members disclosed in FIG. 11. In this case, while the outer shapes of the trapping structural members 1 can be made the same, the number of the trapping structural members in each column and the intervals of the centers of the structural members are changed. Obviously, it is possible to substitute a part of the configurations of FIGS. 22 to 24 with another configuration, to add another configuration to one configuration, or to add, delete, or substitute another configuration with respect to one configuration.

Figure 25:
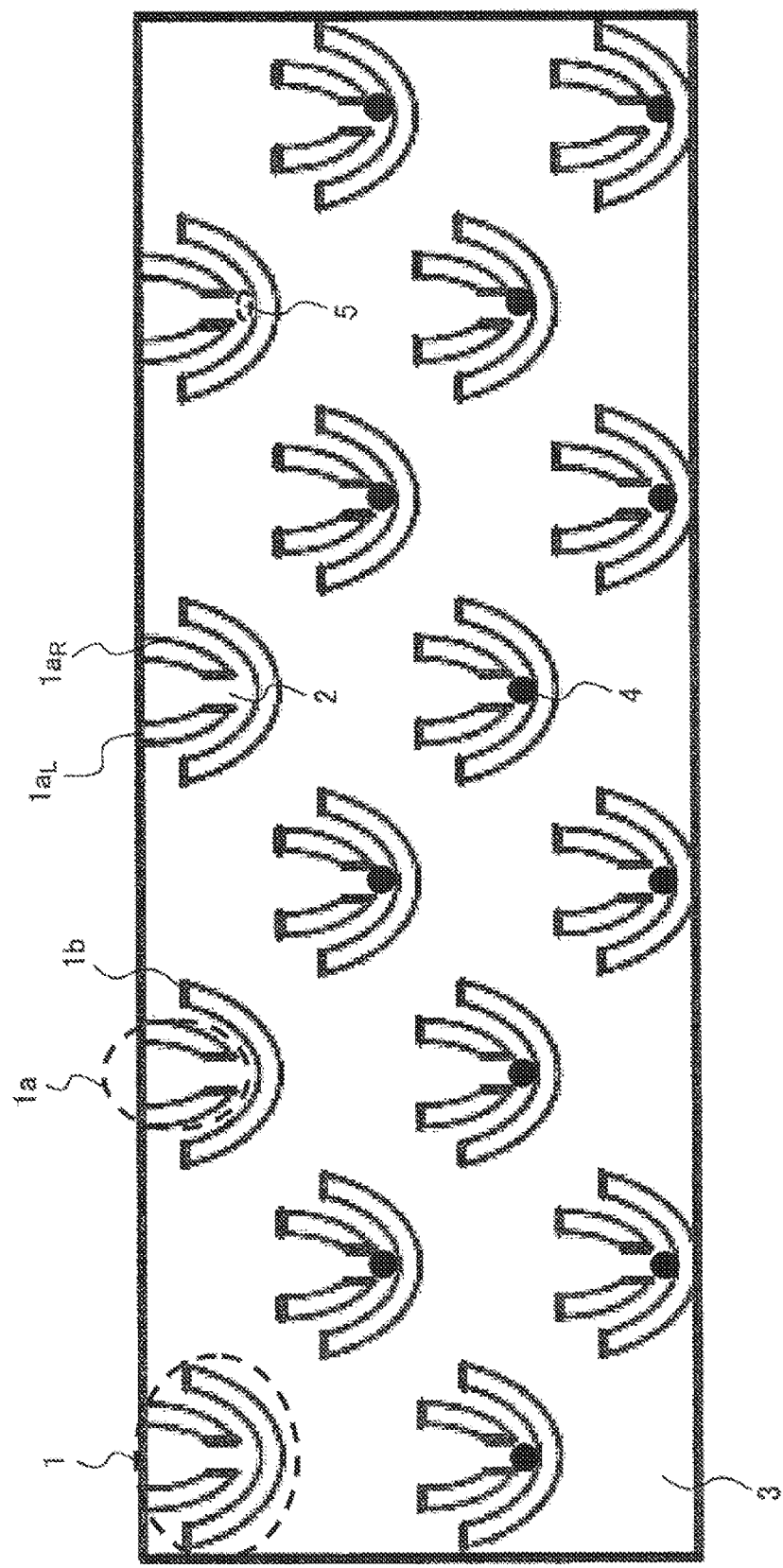
FIG. 25 is a schematic diagram of an example of the trapping structural members.

FIG. 25 illustrates a case where the size of the bio-related substances 4 is smaller than the width of the slit 2 but is larger than the gaps at the two locations between the structural member 1a with a slit and the structural member 1b without a slit. When this condition is satisfied, the bio-related substances 4 can pass the slit 2 but cannot pass the gaps at the two locations between the structural member 1a with a slit and the structural member 1b without a slit. Thus, the bio-related substances 4 are reliably trapped in the trapping structural members 1. Once the bio-related substances 4 are trapped in the trapping structural members 1, the gaps at the two locations between the structural member 1a with a slit and the structural member 1b without a slit are partially blocked, whereby the Trap rate (/width) is decreased compared with before the bio-related substances 4 are trapped. As a result, the probability of a plurality of bio-related substances 4 being trapped in the same trapping structural members 1 is decreased, so that single bio-related substances 4 can be trapped in a number of trapping structural members 1. The present method is believed to be effective when the minor axis of the bio-related substances 4 is preferably 5 µm or more, and may therefore be applied to cells in general. Particularly, the method may be applied to cancer cells in blood, such as circulating tumor cells (CTC), with small deformation compared with blood cells or stem cells (iPS, ES cell). Further, when trapped, the trap rate is greatly decreased. On the other hand, in FIG. 1, the size of the bio-related substances 4 is smaller than the width of the slit 2 and the gaps at the two locations between the structural member 1a with a slit and the structural member 1b without a slit, so that not all of the bio-related substances 4 are trapped but they are trapped with a certain probability in the dead water region 5.

Figure 26:
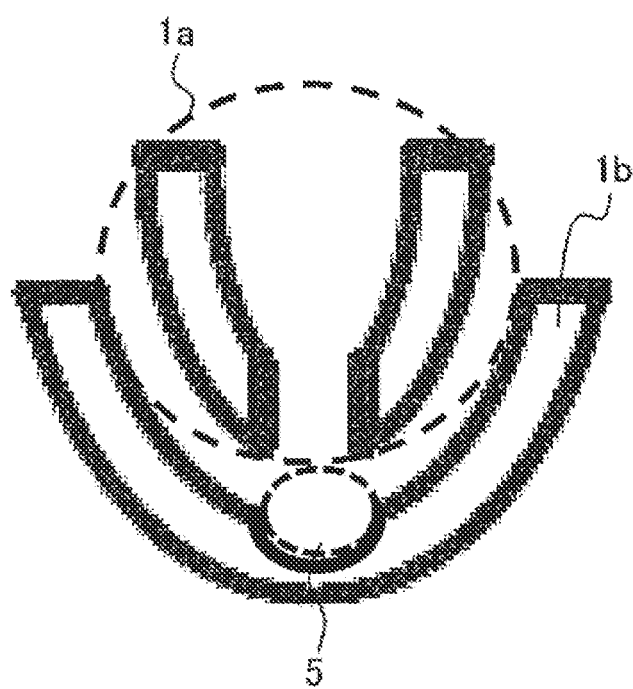
FIG. 26 is a schematic diagram of an example of the trapping structural member with an expanded dead water region.

In FIG. 26, the structural member 1b without a slit is provided with a recess for increasing the dead water region 5. In this way, the trap rate of the bio-related substance that has passed the slit can be increased.

Figure 27:
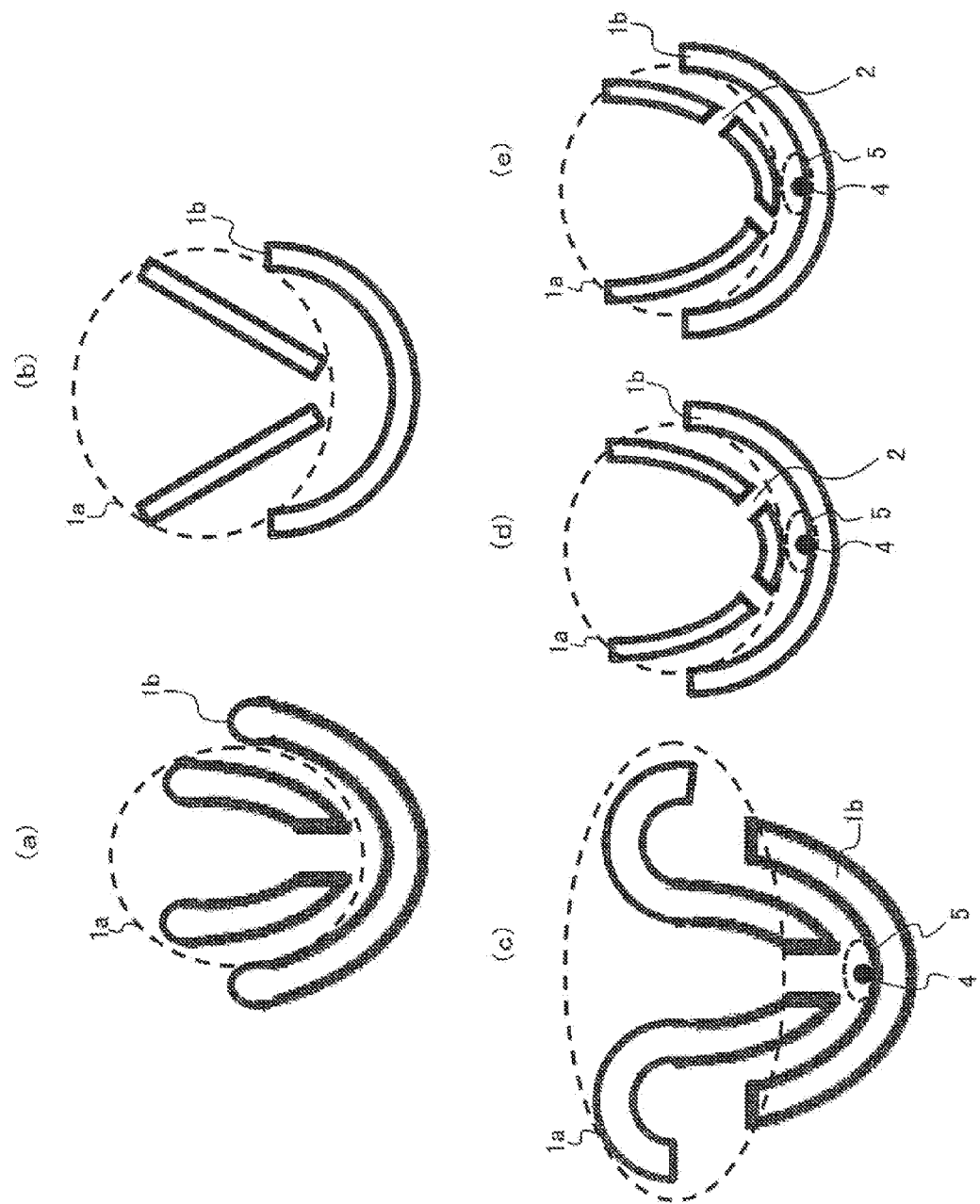
FIG. 27 is a schematic diagram of modifications of the trapping structural member.

FIG. 27 illustrates modifications of the trapping structural members. In FIG. 27(a), the structural member 1a with a slit and the structural member 1b without a slit are rounded to make some of their apexes smooth. The rounding provides the effect of, e.g., eliminating the separation of fluid flow. Because a flow stabilizing shape can be realized by using flow simulation and the like, it is also possible to streamline the slit portion in FIG. 27(a). FIG. 27(b) illustrates a trapping structural member such that the structural member 1a with a slit comprises a part of a triangle. Thus, the shape of the structural member 1a with a slit and the structural member 1b without a slit may comprise an arc, an elliptic arc, or a part of a triangle. Other shapes, such as a hyperbola, may also be incorporated as needed. In FIG. 27(c), the structural member 1a with a slit is provided with two semicircle shapes to collect the bio-related substances 4. By adding the semicircle shapes, when the solution is sent from the structural member 1b without a slit toward the structural member 1a with a slit, the solution can be sent from the dead water region 5 toward the structural member 1a with a slit, whereby the bio-related substances 4 can be collected. On the other hand, in the absence of the semicircle shapes, the solution cannot be sent from the dead water region 5 toward the structural member 1a with a slit, making it difficult to collect the bio-related substances 4. FIG. 27(d) illustrates a case where the structural member 1a with a slit has two slits. In this case too, the bio-related substances 4 can be trapped in the dead water region 5. While the slits 2 are positioned line-symmetrically with respect to the structural member 1a with a slit, the slits 2 may be placed at positions that are not line-symmetric, as illustrated in FIG. 27(e). This is effective when, e.g., the flow volume is different between the gaps at the two locations between the structural member 1a with a slit and the structural member 1b without a slit.

REFERENCE SIGNS LIST

1 Trapping structural member
1a Structural member with a slit
1$a_L$ Left side of the structural member with a slit
1$a_R$ Right side of the structural member with a slit
1b Structural member without a slit
2, 2a, 2b Slit
3, 34 Flow passageway
4 Bio-related substance
5 Dead water region
11 Reagent container
12 Reagent rack
13 Reagent rack base
14 Pre-mix container
20 Sampling nozzle
21 Guide rail
22 Linear movement unit
23 Rotating shaft
24 Arm
30 Flow cell
31 Flow cell stage
32 Injection port
33 Discharge port
36 Upper substrate
37 Lower substrate
38 Spacer
40 Detection unit
41 Light source
42 Imaging device
50 Control/computation unit
51 Input unit
52 Display unit
53 Fluid level sensing unit
60 Microsyringe
61 Plunger 62 First flow passageway
63 Second flow passageway
64 Washing fluid tank
65 Pump
66 Washing fluid circulation flow passageway
67 Flow volume adjustment aperture
68 Washing tank
69 Waste fluid tank
71 First electromagnetic valve
72 Second electromagnetic valve

The invention claimed is:

1. A flow cell used for analyzing a bio-related substance, the flow cell comprising:
   a flow passageway, and an injection opening and a discharge opening that are connected to the flow passageway,
   wherein the flow passageway is provided with a trapping structural member that traps the bio-related substance, the trapping structural member including a structure forming a dead water region in which the bio-related substance is trapped,
   wherein the trapping structural member includes a slit member having a slit that passes the bio-related substance, and an accommodating member disposed on a downstream side of the slit member and facing the slit member to accommodate the bio-related substance.

2. The flow cell according to claim 1, wherein the accommodating member has a U-shaped curved shape.

3. The flow cell according to claim 2, wherein the accommodating member includes a recess at a position facing the slit.

4. The flow cell according to claim 1, wherein:
   the trapping structural member is arranged in a matrix including a fluid of flow direction and a direction perpendicular to the fluid flow direction;
   the trapping structural member is disposed at regular intervals in a row direction; and
   a trapping structural member of an odd-numbered row is placed at substantially the center of adjacent trapping structural members placed at even-numbered rows.

5. The flow cell according to claim 1, wherein that the trapping structural member has a height equal to a height of the flow passageway.

6. The flow cell according to claim 1, wherein:
   the trapping structural member includes a pair of parallel curved waveform structural members, the curved waveform shape having periodicity, the waveform of each period being symmetrical; and
   one of the pair of structural members includes a slit on an upper end, and the other includes a slit on a lower end, each of the slits having a predetermined interval.

7. The flow cell according to claim 1, wherein the trapping structural member has an increasingly higher trap rate toward the downstream side.

8. The flow cell according to claim 7, wherein the trapping structural member has an increasingly greater size toward the downstream side.

9. The flow cell according to claim 7, wherein the slit member has an increasingly greater slit interval toward the downstream side.

10. The flow cell according to claim 8, wherein the trapping structural member has an increasingly greater number of rows toward the downstream side.

11. An analysis method for analyzing a bio-related substance using a flow cell including a flow passageway and an injection opening and a discharge opening that are connected to the flow passageway,
    wherein the method comprises a step of forming a dead water region by a trapping structural member disposed in the flow passageway to trap the bio-related substance, wherein the trapping structural member includes a slit member having a slit that passes the bio-related substance, and an accommodating member disposed on a downstream side of the slit member and facing the slit member to accommodate the bio-related substance, and the slit has a large interval with respect to the bio-related substance, the interval being greater than the interval of a gap between the slit member and the accommodating member;
    and a step of trapping the bio-related substance in the dead water region.

12. The analysis method according to claim 11, wherein the bio-related substance is a bacterium, a cell, or a bound body of at least one of the bacterium and the cell and a fine particle.

13. The analysis method according to claim 11, wherein the method comprises a step of detecting the trapped bio-related substance.

14. The analysis method according to claim 13, wherein the step of detecting uses Raman, a bright field, a dark field, a phase difference, differential interference, fluorescence, light emission, or an electronic microscope.

15. The analysis method according to claim 13, wherein the method comprises, after the step of detecting, a step of collecting the bio-related substance by varying a solution sending speed, or the solution sending speed and a solution sending direction.

16. An analysis device used for analyzing a bio-related substance, the analysis device comprising:
    a flow cell including a flow passageway and an injection opening and a discharge opening that are connected to the flow passageway;
    an injection mechanism that injects a sample via the injection opening; and
    a detection mechanism that detects the bio-related substance trapped in the flow cell,
    wherein the flow passageway is provided with a trapping structural member that traps the bio-related substance, wherein the trapping structural member includes a structure forming a dead water region in which the bio-related substance is trapped, and wherein the trapping structural member includes a slit member having a slit that passes the bio-related substance, and an accommodating member disposed on a downstream side of the slit member and facing the slit member to accommodate the bio-related substance.

* * * * *